United States Patent [19]

Hioki et al.

[11] Patent Number: 5,538,843
[45] Date of Patent: * Jul. 23, 1996

[54] HYDRAZINE COMPOUND AND SILVER HALIDE PHOTOGRAPHIC MATERIAL CONTAINING THE SAME

[75] Inventors: Takanori Hioki; Tadashi Ikeda, both of Kanagawa, Japan

[73] Assignee: Fuji Photo Film Co., Ltd., Kanagawa, Japan

[ * ] Notice: The portion of the term of this patent subsequent to Sep. 21, 2014, has been disclaimed.

[21] Appl. No.: 337,475

[22] Filed: Nov. 8, 1994

[30] Foreign Application Priority Data

Nov. 10, 1993 [JP] Japan .................... 5-303307

[51] Int. Cl.$^6$ .................................... G03C 1/34
[52] U.S. Cl. .................................... 430/614; 430/570
[58] Field of Search .................... 430/264, 570, 430/598, 607, 614

[56] References Cited

U.S. PATENT DOCUMENTS

| | | | |
|---|---|---|---|
| 5,006,445 | 4/1991 | Yagihara et al. | 430/264 |
| 5,100,761 | 3/1992 | Yagihara et al. | 430/264 |
| 5,190,853 | 3/1993 | Seto et al. | 430/264 |
| 5,300,419 | 4/1994 | Seto et al. | 430/607 |
| 5,340,694 | 8/1994 | Hioki et al. | 430/264 |

FOREIGN PATENT DOCUMENTS

| | | | |
|---|---|---|---|
| 61-91658 | 5/1986 | Japan . | |
| 5216152 | 8/1993 | Japan | G03C 1/12 |

OTHER PUBLICATIONS

Chemical Abstracts 105:162195.
The Theory of the Photographic Process, pp. 259–265 and pp. 265–268 (Macmillan, 1966).
Journal of the Physical Chemistry, vol. 94, p. 1298 (1990).

*Primary Examiner*—Janet C. Baxter
*Attorney, Agent, or Firm*—Sughrue, Mion, Zinn, Macpeak & Seas

[57] ABSTRACT

A silver halide photographic material comprising a support having thereon a silver halide emulsion layer which comprises a hydrazine compound having at least one absorbent group to silver halide, wherein two nitrogen atoms of the hydrazine compound are substituted by four substituents and the carbon atoms in the four substituents bonded directly to the two nitrogen atoms are not substituted by an oxo group.

14 Claims, No Drawings

1

HYDRAZINE COMPOUND AND SILVER HALIDE PHOTOGRAPHIC MATERIAL CONTAINING THE SAME

FIELD OF THE INVENTION

The present invention relates to a silver halide photographic material having a high sensitivity and an excellent storage stability.

The present invention also relates to a novel compound.

BACKGROUND OF THE INVENTION

Silver halide photographic materials have hitherto been demanded to have a high sensitivity. In particular, spectrally sensitized silver halide photographic materials have keenly demanded to have a high sensitivity.

The spectral sensitization is a very important and essential technique in the production of a light-sensitive material having a high sensitivity and an excellent color reproducibility. The spectral sensitizer has a function to absorb light in a long wavelength region where the silver halide photographic emulsion inherently does not absorb light in a substantial sense and to transmit the light absorption energy to the silver halide. The increased amount of light captured by the spectral sensitizer is advantageous to enhance the photographic sensitivity. Accordingly, it has been attempted to increase the captured light amount by increasing the amount of the spectral sensitizer added to a silver halide emulsion. However, if the spectral sensitizer is added to a silver halide emulsion in an amount exceeding the optimum range, the sensitivity is, on the contrary, greatly reduced. This is generally called as dye desensitization and is a phenomenon that desensitization occurs in the region to which the silver halide is inherently light-sensitive and where the sensitizing dye absorbs substantially no light. If the dye desensitization is large, the spectral sensitization effect may be provided but overall sensitivity is reduced. In other words, with the reduction in dye desensitization, the sensitivity in the region where the sensitizing dye absorbs light (namely, spectral sensitivity) increases correspondingly. Therefore, the improvement in dye desensitization is a great subject in the spectral sensitization technique. The dye desensitization is larger as the sensitizing dye has its light-sensitive region at a longer wavelength. This is described in T. H. James, *The Theory of the Photographic Process*, pp. 265–268 (Macmillan, 1966).

Further, as described in T. Tani et al, *Journal of the Physical Chemistry*, Vol. 94, p. 1298 (1990), sensitizing dyes having a reduction potential more noble than −1.25 V are known to provide a low relative quantum yield in spectral sensitization. In order to increase the relative quantum yield of such a dye in spectral sensitization, supersensitization by capturing positive holes has been proposed as described in the above-described *The Theory of the Photographic Process*, pp. 259–265 (1966).

In order to solve the above-described desensitization, JP-A-5-216152 (the term "JP-A" as used herein means an "unexamined published Japanese patent application") describes hydrazine compounds having a specific structure.

However, still higher sensitivity and more improved storage stability have been demanded.

SUMMARY OF THE INVENTION

An object of the present invention is to provide a highly sensitive silver halide photographic material.

Another object is to provide a silver halide photographic material having a high storage stability.

Further object is to provide a novel compound.

The above-described objects of the present invention have been achieved by a silver halide photographic material comprising at least one hydrazine compound having at least one adsorption group to silver halide, more preferably at least one compound represented by the following formula (I)

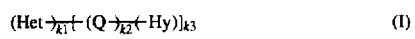

wherein Het represents a group having a 5-, 6- or 7-membered heterocyclic ring which contains at least one nitrogen atom and may contain a hetero atom other than a nitrogen atom, Q represents a divalent linking group composed of an atom or an atomic group containing at least one of a carbon atom, a nitrogen atom, a sulfur atom and an oxygen atom, Hy represents an atomic group having a hydrazine structure represented by formula (II), k1 and k3 each represents 1, 2, 3 or 4, and k2 represents 0 or 1,

wherein $R_1$, $R_2$, $R_3$ and $R_4$ each represents an alkyl group, an aryl group or a heterocyclic group, with the proviso that the carbon atom bonded directly to the nitrogen atom of hydrazine represented by Hy is not substituted by an oxo group.

The above-described objects have been achieved by the compound represented by formula (I) above.

More preferably, these have been achieved by a spectrally sensitized silver halide photographic material containing a hydrazine compound represented by formula (I).

DETAILED DESCRIPTION OF THE INVENTION

The present invention will be described below in more detail.

As the adsorption group to silver halide, preferred is a group having the following partial structure, and having a 5-, 6- or 7-membered heterocyclic ring which contains at least one nitrogen atom and may contain a hetero atom other than a nitrogen atom (e.g., oxygen, sulfur, selenium, tellurium).

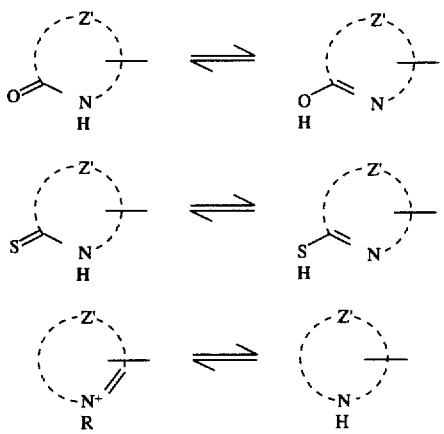

wherein Z represents an atomic group necessary for forming a nitrogen-containing heterocyclic ring, and R represents an aliphatic group.

The hydrazine structure represented by formula (II), which is used preferably as Hy, will be described in detail.

In the formula, $R_1$, $R_2$, $R_3$ and $R_4$ each represents an alkyl group, an aryl group or a heterocyclic group. $R_1$ and $R_2$, $R_3$ and $R_4$, $R_1$ and $R_3$, or $R_2$ and $R_4$ may combine with each other to form a ring butt do not form an aromatic ring.

In $R_1$, $R_2$, $R_3$ and $R_4$, the carbon atom directly bonded to the nitrogen atom of hydrazine is not substituted by an oxo The hydrazine compound represented by formula (II) is substituted by at least one $—(Q)_{k2}—(Het)_{k1}$.

The compound represented by formula (II) is particularly preferably a compound selected from those represented by formulae (III), (IV) and (V) for achieving high sensitivity.

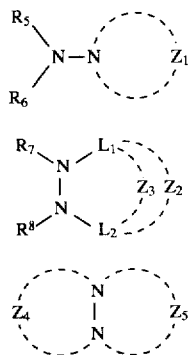

(III)

(IV)

(V)

In the formulae, $R_5$, $R_6$, $R_7$ and $R_8$ each represents an alkyl group, an aryl group or a heterocyclic group.

$Z_1$ represents an alkylene group having 4 or 6 carbon atoms.

$Z_2$ represents an alkylene group having 2 carbon atoms.

$Z_3$ represents an alkylene group having 1 or 2 carbon atoms.

$Z_4$ and $Z_5$ each represents an alkylene group having 3 carbon atoms.

$L_1$ and $L_2$ each represents a methine group.

In $R_5$, $R_6$, $R_7$, $R_8$, $Z_1$, $Z_4$ and $Z_5$, the carbon atom directly bonded to the nitrogen atom of hydrazine is not substituted by an oxo group.

The compounds of formulae (III), (IV) and (V) are each substituted by at least one $—(Q)_{k2}—(Het)_{k1}$.

The compounds represented by formula (III) and (IV) are more preferred and the compound represented by formula (III) is particularly preferred.

Formula (II) will be described below in detail.

$R_1$, $R_2$, R3 and $R_4$ each preferably represents an unsubstituted alkyl group (e.g., methyl, ethyl, propyl, isopropyl, butyl, isobutyl, hexyl, octyl, dodecyl, octadecyl, cyclopentyl, cyclopropyl, cyclohexyl); a substituted alkyl group {when the substituent is expressed by V, the substituent represented by V is not particularly limited; examples thereof include a carboxyl group, a sulfo group, a cyano group, a halogen atom (e.g., fluorine, chlorine, bromine, iodine), a hydroxyl group, an alkoxycarbonyl group (e.g., methoxycarbonyl, ethoxycarbonyl, phenoxycarbonyl, benzyloxycarbonyl), an alkoxy group (e.g., methoxy, ethoxy, benzyloxy, phenethyloxy), an aryloxy group having 18 or less carbon atoms (e.g., phenoxy, 4-methylphenoxy, α-naphthoxy), an acyloxy group (e.g., acetyloxy, propionyloxy), an acyl group (e.g., acetyl, propionyl, benzoyl, mesyl), a carbamoyl group (e.g., carbamoyl, N,N-dimethylcarbamoyl, morpholinocarbonyl, piperidinocarbonyl), a sulfamoyl group (e.g., sulfamoyl, N,N-dimethylsulfamoyl, morpholinosulfonyl, piperidinosulfonyl), an aryl group (e.g., phenyl, 4-chlorophenyl, 4-methylphenyl, α-naphthyl), a heterocyclic group (e.g., 2-pyridyl, tetrahydrofurfuryl, morpholino, 2-thienyl), an amino group (e.g., amino, dimethylamino, anilino, diphenylamino), an alkylthio group (e.g., methylthio, ethylthio), an alkylsulfonyl group (e.g.,methylsulfonyl, propylsulfonyl), an alkylsulfinyl group (e.g., methylsulfinyl), a nitro group, a phosphate group, an acylamino group (e.g., acetylamino), an ammonium group (e.g., trimethylammonium, tributylammonium), a mercapto group, a hydrazino group (e.g., trimethylhydrazino), a ureido group (e.g., ureido, N,N-dimethylureido), an imide group and an unsaturated hydrocarbon group (e.g., vinyl, ethynyl, 1-cyclohexenyl, benzylidine, benzylidene); the substituent V preferably has 18 or less carbon atoms; the substituent may further be substituted by V; and more specific examples thereof include an alkyl group (e.g., carboxymethyl, 2-carboxyethyl, 3-carboxypropyl, 4-carboxybutyl, 2-sulfoethyl, 3-sulfopropyl, 4-sulfobutyl, 3-sulfobutyl, 2-hydroxy-3-sulfopropyl, 2-cyanoethyl, 2-chloroethyl, 2-bromoethyl, 2-hydroxyethyl, 3-hydroxypropyl, hydroxymethyl, 2-hydroxyethyl, 2-methoxyethyl, 2-ethoxyethyl, 2-ethoxycarbonylethyl, methoxycarbonylmethyl, 2-methoxyethyl, 2-ethoxyethyl, 2-phenoxyethyl, 2-acetyloxyethyl, 2-propionyloxyethyl, 2-acetylethyl, 3-benzoylpropyl, 2-carbamoylethyl, 2-morpholinocarbonylethyl, sulfamoylmethyl, 2-(N,N-dimethylsulfamoyl)ethyl, benzyl, 2-naphthylethyl, 2-(2-pyridyl)ethyl, allyl, 3-aminopropyl, 3-dimethylaminopropyl, methylthiomethyl, 2-methylsulfonylethyl, methylsulfinylmethyl, 2-acetylaminoethyl, 3-trimethylammonium ethyl, 2-mercaptoethyl, 2-trimethylhydrazinoethyl, methylsulfonylcarbamoylmethyl and (2-methoxy)ethoxymethyl}; an aryl group (e.g., phenyl, α-naphthyl, β-naphthyl, phenyl substituted, for example, by the above-described substituent V, naphthyl); or a heterocyclic group (e.g., 2-pyridyl, 2-thiazolyl, 2-pyridyl substituted by the above-described substituent V).

$R_1$ and $R_2$, $R_3$ and $R_4$, $R_1$ and $R_3$, or $R_2$ and $R_4$ may combine with each other to form a ring other than an aromatic ring. The ring may be substituted, for example, by the above-described substituent V.

In $R_1$, $R_2$, $R_3$ and $R_4$, the carbon atom directly bonded to the nitrogen atom of hydrazine is not substituted by an oxo group. For example, $R_1$, $R_2$, $R_3$ and $R_4$ each is not an acetyl group, a carboxyl group, a benzoyl group or a formyl group, and if a ring is formed by two of them, not a malonyl group, a succinyl group, a glutaryl group or an adipoyl group.

In $R_1$, $R_2$, $R_3$ and $R_4$, the carbon atom directly bonded to the nitrogen atom of hydrazine is preferably not substituted by a thioxo group (e.g., thiaacetyl, thioaldehyde, thiocarboxyl, thiobenzoyl).

$R_1$, $R_2$, $R_3$ and $R_4$ each more preferably represents the above-described unsubstituted alkyl group or substituted alkyl group, and $R_1$ and $R_2$, $R_3$ and $R_4$, $R_1$ and $R_3$, or $R_2$ and $R_4$ combine together more preferably to form an alkylene group {the alkylene group may be substituted (for example, by the above-described substituent V)} containing no atom (e.g., oxygen, sulfur, nitrogen) other than a carbon atom as the constituent of the ring.

$R_1$, $R_2$, $R_3$ and $R_4$ each still more preferably represents a group when the carbon atom directly bonded to the nitrogen atom of hydrazine is in an unsubstituted methylene group or a methylene group substituted by an alkyl group (e.g., methyl, ethyl), particularly preferably represents an unsubstituted alkyl group (e.g., methyl, ethyl, propyl, butyl), a substituted alkyl group (for example, a sulfoalkyl group (e.g., 2-sulfoethyl, 3-sulfopropyl, 4-sulfobutyl, 3-sulfobutyl), a carboxyalkyl group (e.g., carboxymethyl, 2-carboxyethyl), a hydroxyalkyl group (e.g., 2-hydroxyethyl)} or a group when $R_1$ and $R_2$, $R_3$ and $R_4$, $R_1$ and $R_3$, or $R_2$ and $R_4$ is combined with each other to form a 5- or 7-membered ring through an alkylene chain.

The hydrazine structure represented by formula (II) is substituted by at least one —$(Q)_{k2}$—$(Het)_{k1}$. The position to substitute may be any of $R_1$, $R_2$, $R_3$ and $R_4$.

The hydrazine compound represented by formula (II) may be freely isolated as a salt if it is advantageous in the synthesis or the storage. In this case, any compound may be used as long as the compound can form a salt with a hydrazine and preferred examples of the salt include arylsulfonate (e.g., p-toluenesulfonate, p-chlorobenzenesulfonate), aryldisulfonate (e.g., 1,3-benzenedisulfonate, 1,5-naphthalenedisulfonate, 2,6-naphthalenedisulfonate), thiocyanate, picrate, carboxylate (e.g., oxalate, acetate, benzoate, hydrogenoxalate), a halogen acid salt (e.g., hydrochlorate, hydrofluorate, hydrobromate, hydroiodate), sulfate, perchlorate, tetrafluoroborate, sulfite, nitrate, phosphate, carbonate and bicarbonate.

Of these, preferred are hydrogenoxalate, oxalate and hydrochlorate.

Formula (III) will be described below in detail.

$R_5$ and $R_6$ each has the same meaning and preferred embodiment as $R_1$, $R_2$, $R_3$ or $R_4$.

Particularly preferably, $R_5$ and $R_6$ each represents an alkyl group or combine with each other to from an unsubstituted tetramethylene group.

$Z_1$ represents an alkylene group having 4 or 6 carbon atoms, more preferably an alkylene group having 4 carbon atoms.

The carbon atom bonded directly to the nitrogen atom of hydrazine is not substituted by an oxo group.

The alkylene group may be either unsubstituted or substituted and examples of the substitute include the above-described groups for the substituent V, however, the carbon atom bonded directly to the nitrogen atom of hydrazine is preferably in an unsubstituted methylene group or a methylene group substituted by an alkyl group (e.g., methyl, ethyl).

$Z_1$ particularly preferably represents an unsubstituted tetramethylene group.

The hydrazine structure represented by formula (III) is substituted by at least one —$(Q)_{k2}$—$(Het)_{k1}$. The position to substitute may be any of $R_5$, $R_6$ and $Z_1$, but preferably, it is $R_5$ or $R_6$.

Formula (IV) will be described below in detail.

$R_7$ and $R_8$ each has the same meaning and preferred embodiment as $R_1$, $R_2$, $R_3$ or $R_4$.

Particularly preferably, $R_7$ and $R_8$ each represents an alkyl group or combine with each other to form a trimethylene group.

$Z_2$ represents an alkylene group having 2 carbon atoms.

$Z_3$ represents an alkylene group having 1 or 2 carbon atoms.

These alkylene groups may be either unsubstituted or substituted and examples of the substituent include the above-described groups for the substituent V.

$Z_2$ more preferably represents an unsubstituted ethylene group.

$Z_3$ more preferably represents an unsubstituted methylene or ethylene group.

$L_1$ and $L_2$ each represents a substituted or unsubstituted methine group. Examples of the substituent include the above-described groups for the substituent V and preferred examples thereof include an unsubstituted alkyl group (e.g., methyl, t-butyl).

Still more preferred is an unsubstituted methine group.

The hydrazine structure represented by formula (IV) is substituted by at least one —$(Q)_{k2}$—$(Het)_{k1}$ and the position to substitute may be any of $R_7$, $R_8$, $Z_2$, $Z_3$, $L_1$ and $L_2$ but preferably, it is $R_7$ or $R_8$.

Formula (V) will be described below in detail.

$Z_4$ and $Z_5$ each represents an alkylene group having 3 carbon atoms.

The carbon atom directly bonded to the nitrogen atom of hydrazine is not substituted by an oxo group.

The alkylene group may be either unsubstituted or substituted. Examples of the substituent include the above-described groups for the substituent V and the carbon atom directly bonded to the nitrogen atom of hydrazine is preferably in an unsubstituted methylene group or a methylene group substituted by an alkyl group (e.g., methyl, ethyl).

$Z_4$ and $Z_5$ each particularly preferably represents an unsubstituted trimethylene group, an unsubstituted alkyl group or a substituted trimethylene group (e.g, 2,2-dimethyltrimethylene).

The hydrazine structure represented by formula (I) is substituted by at least one —$(Q)_{k2}$—$(Het)_{k1}$. The position to substitute may be either $Z_4$ or $Z_5$.

The compound represented by formula (III), (IV) or (V) may be freely isolated as a salt the same as the compound represented by formula (I). Examples of the salt include those set forth for the salt of formula (I). Preferred are hydrogenoxalate, oxalate and hydrochlorate.

Formula (I) will be described in detail.

The group represented by Het may be any as long as it contains at least one nitrogen atom and has a 5-, 6- or 7-membered hetero ring which may have a hetero atom (e.g., oxygen, sulfur, selenium, tellurium) other than a nitrogen atom. Preferred examples thereof include an azole ring (e.g., imidazole, triazole, tetrazole, thiazole, oxazole, selenazole, benzimidazole, benzotriazole, indazole, benzoxazole, benzothiazole, thiadiazole, oxadiazole, benzoselenazole, pyrazole, naphthothiazole, naphthoimidazole, naphthoxazole, azabenzimidazole, purine), a pyrimidine ring, a triazine ring and an azaindene ring (e.g., triazaindene, tetrazaindene, pentazaindene).

The nitrogen-containing heterocyclic compound is more preferably represented by formula (VI), (VII), (VIII), (IX), (X), (XI) or (XII).

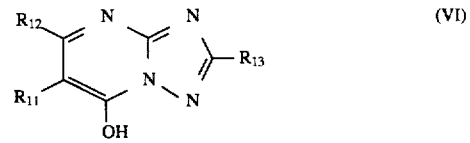

(VI)

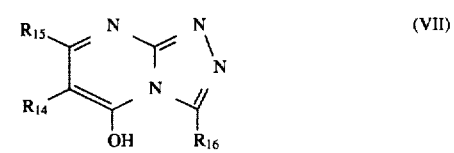

(VII)

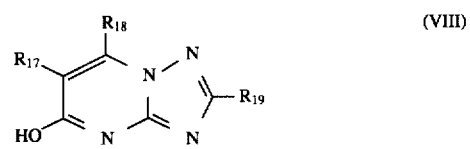

(VIII)

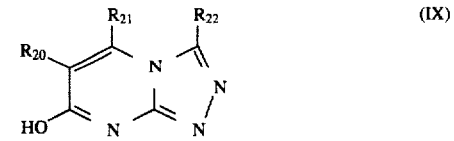

(IX)

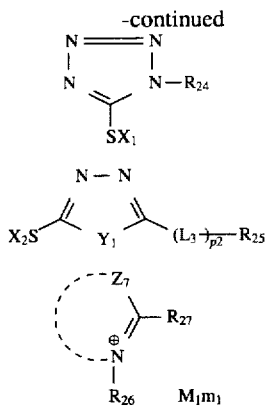

(X)

(XI)

(XII)

In the formulae, $R_{11}$, $R_{12}$, $R_{13}$, $R_{14}$, $R_{15}$, $R_{16}$, $R_{17}$, $R_{18}$, $R_{19}$, $R_{20}$, $R_{21}$ and $R_{22}$ each represents a hydrogen atom or a monovalent substituent.

$R_{24}$ represents an alkyl group, an aryl group or a heterocyclic group.

$X_1$ represents a hydrogen atom, an alkali metal atom, an ammonium group or a precursor thereof.

$Y_1$ represents an oxygen atom, a sulfur atom, =NH, =N—$(L_4)_{p_3}$—$R_{28}$.

$L_3$ and $L_4$ each represents a divalent linking group.

$R_{25}$ and $R_{28}$ each represents a hydrogen atom, an alkyl group, an aryl group or a heterocyclic group.

$X_2$ has the same meaning as $X_1$.

$p_2$ and $p_3$ each represents an integer of 0 or more, preferably an integer of 0 to 3.

$Z_7$ represents an atomic group necessary for forming a 5- or 6-membered nitrogen atom-containing heterocyclic ring.

$R_{26}$ and $R_{27}$ each represents a hydrogen atom or an alkyl group.

The compounds represented by formula (VI), (VII), (VIII), (IX), (X), (XI) and (XII) each are substituted by at least one —$(Q)_{k2}$—(Hy).

Among formulae (VI) to (XII), preferred are formulae (VI) and (X) and more preferred is formula (X).

Formulae (VI), (VII), (VIII), (IX), (X), (XI) and (XII) will be described below in more detail.

$R_{11}$, $R_{12}$, $R_{13}$, $R_{14}$, $R_{15}$, $R_{16}$, $R_{17}$, $R_{18}$, $R_{19}$, $R_{20}$, $R_{21}$, and $R_{22}$ each represents a hydrogen atom or a monovalent substituent. Examples of the monovalent substituent include substituents set forth above as preferred examples for $R_1$, $R_2$, $R_3$ and $R_4$.

More preferred examples include a lower alkyl group (preferably substituted or unsubstituted and having from 1 to 4 carbon atoms, e.g., methyl, ethyl, n-propyl, isopropyl, n-butyl, t-butyl, methoxyethyl, hydroxyethyl, hydroxymethyl, vinyl, allyl), a carboxyl group, an alkoxy group (preferably substituted or unsubstituted and having from 1 to 5 carbon atoms, e.g., methoxy, ethoxy, methoxyethoxy, hydroxyethoxy), an aralkyl group (preferably substituted or unsubstituted and having from 7 to 12 carbon atoms, e.g., benzyl, phenethyl, phenylpropyl), an aryl group (preferably substituted or unsubstituted and having from 6 to 12 carbon atoms, e.g., phenyl, 4-methylphenyl, 4-methoxyphenyl), a heterocyclic group (e.g., 2-pyridyl), an alkylthio group (preferably substituted or unsubstituted and having from 1 to 10 carbon atoms, e.g., methylthio, ethylthio), an arylthio group (preferably substituted or unsubstituted and having from 6 to 12 carbon atoms, e.g., phenylthio), an aryloxy group (preferably substituted or unsubstituted and having from 6 to 12 carbon atoms, e.g., phenoxy), an alkylamino group having 3 or more carbon atoms (e.g., propylamino, butylamino), an arylamino group (e.g., anilino), a halogen atom (e.g., chlorine, bromine, fluorine) and the following substituents.

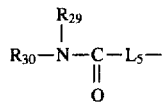

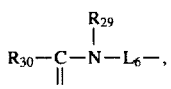

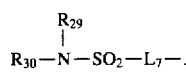

In the above, $L_5$, $L_6$ and $L_7$ each is a linking group and represents an alkylene group (preferably having from 1 to 5 carbon atoms, e.g., methylene, propylene, 2-hydroxypropylene).

$R_{29}$ and $R_{30}$ may be the same or different and each represents hydrogen atom, an alkyl group (preferably a substituted or unsubstituted and having from 1 to 10 carbon atoms, e.g., methyl, ethyl, n-propyl, isopropyl, n-butyl, t-butyl, n-octyl, methoxyethyl, hydroxyethyl, allyl, propargyl), an aralkyl group (preferably substituted or unsubstituted and having from 7 to 12 carbon atoms, e.g., benzyl, phenethyl, vinylbenzyl), an aryl group (preferably substituted or unsubstituted and having from 6 to 12 carbon atoms, e.g., phenyl, 4-methylphenyl), or a heterocyclic group (e.g., 2-pyridyl).

$R_{24}$ has the same meaning and preferred embodiment as $R_1$, $R_2$, $R_3$ or $R_4$.

The alkyl group, aryl group or heterocyclic group for $R_{24}$ may be either unsubstituted or substituted.

Examples of the substituent include substituents set forth above as preferred examples for $R_1$, $R_2$, $R_3$ and $R_4$.

More preferred examples include a halogen atom (e.g., chlorine, bromine, fluorine), a nitro group, a cyano group, a hydroxyl group, an alkoxy group (e.g., methoxy), an aryl group (e.g., phenyl), an acylamino group (e.g., propionylamino), an alkoxycarbonylamino group (e.g., methoxycarbonylamino), a ureido group, an amino group, a heterocyclic group (e.g., 2-pyridyl), an acyl group (e.g., acetyl), a sulfamoyl group, a sulfonamide group, a thioureido group, a carbamoyl group, an alkylthio group (e.g., methylthio), an arylthio group (e.g., phenylthio), a heterocyclic thio group (e.g., 2-benzothiazolylthio), a carboxylic acid group, a sulfonic acid group and a salt thereof.

The above-described ureido group, thioureido group, sulfamoyl group, carbamoyl group each may be unsubstituted, N-alkyl-substituted or N-aryl-substituted. Examples of the aryl group include a phenyl group or a substituted phenyl group. Examples of the substituent therefor include substituents set forth above as preferred examples for $R_1$, $R_2$, $R_3$ and $R_4$.

Examples of the alkali metal atom represented by $X_1$ or $X_2$ include sodium atom or potassium atom and examples of the ammonium group therefor include tetramethylammonium and trimethylbenzylammonium. The precursor means a group capable of being converted to hydrogen atom, an alkali metal or ammonium and examples thereof include an acetyl group, a cyanoethyl group and a methanesulfonylethyl group.

Specific examples of the divalent linking group represented by $L_3$ or $L_4$ include the following linking groups or combinations thereof.

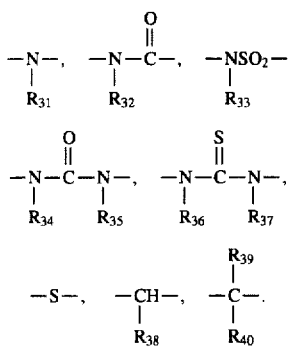

$R_{31}$, $R_{32}$, $R_{33}$, $R_{34}$, $R_{35}$, $R_{36}$, $R_{37}$, $R_{38}$, $R_{39}$ and $R_{40}$ each represents a hydrogen atom, an alkyl group (preferably substituted or unsubstituted and having from 1 to 4 carbon atoms, e.g., methyl, ethyl, n-butyl, methoxyethyl, hydroxyethyl, allyl) or an aralkyl group (preferably substituted or unsubstituted and having from 7 to 12 carbon atoms, e.g., benzyl, phenethyl, phenylpropyl).

$R_{25}$ and $R_{28}$ each preferably represents those set forth above for $R_{24}$.

$Z_7$ preferably represents thiazoliums {e.g., thiazolium, 4-methylthiazolium, benzothiazolium, 5-methylbenzothiazolium, 5-chlorobenzothiazolium, 5-methoxybenzothiazolium, 6-methylbenzothiazolium, 6-methoxybenzothiazolium, naphtho[1,2-d]thiazolium, naphtho[2,1-d]thiazolium}, oxazoliums {e.g., oxazolium, 4-methyloxazolium, benzoxazolium, 5-chlorobenzoxazolium, 5-phenylbenzoxazolium, 5-methylbenzoxazolium, naphtho[1,2-d]oxazolium}, imidazoliums {e.g., 1-methylbenzimidazolium, 1-propyl-5-chlorobenzimidazolium, 1-ethyl-5,6-cyclobenzimidazolium), 1-allyl-5-trifluoromethyl-6-chlorobenzimidazolium) or selenazoliums [e.g., benzoselenazolium, 5-chlorobenzoselenazolium, 5-methylbenzoselenazolium, 5-methoxybenzoselenazolium, naphtho[1,2-d]selenazolium].

Particularly preferred are thiazoliums (e.g., benzothiazolium, 5-chlorobenzothiazolium, 5-methoxybenzothiazolium, naphtho[1,2-d]thiazolium).

$R_{26}$ and $R_{27}$ each preferably represents a hydrogen atom, an unsubstituted alkyl group having 18 or less carbon atoms (e.g., methyl, ethyl, propyl, butyl, pentyl, octyl, decyl, dodecyl, octadecyl) or a substituted alkyl group having 18 or less carbon atoms {examples of the substituent include a vinyl group, an alkenyl group having 3 to 8 carbon atoms (e.g., allyl), a sulfo group, a cyano group, a halogen atom (e.g., fluorine, chlorine, bromine), a hydroxyl group, an alkoxycarbonyl group having 8 or less carbon atoms (e.g., methoxycarbonyl, ethoxycarbonyl, phenoxycarbonyl, benzyloxycarbonyl), an alkoxy group having 8 or less carbon atoms (e.g., methoxy, ethoxy, benzyloxy, phenethyloxy), a monocyclic aryloxy group having 10 or less carbon atoms (e.g., phenoxy, p-tolyloxy), an acyloxy group having 3 or less carbon atoms (e.g., acetyloxy, propionyloxy), an acyl group having 8 or less carbon atoms (e.g., acetyl, propionyl, benzoyl, mesyl), a carbamoyl group (e.g., carbamoyl, N,N-dimethylcarbamoyl, morpholinocarbonyl, piperidinocarbonyl), a sulfamoyl group (e.g., sulfamoyl, N,N-dimethylsulfamoyl, morpholinosulfonyl, piperidinosulfonyl) and an aryl group having 10 or less carbon atoms (e.g., phenyl, 4-chlorophenyl, 4-methylphenyl, α-naphthyl)}.

More preferably $R_{26}$ represents an unsubstituted alkyl group (e.g., methyl, ethyl,) or an alkenyl group (e.g., allyl) and $R_{27}$ represents hydrogen atom or an unsubstituted lower alkyl group (e.g., methyl, ethyl).

$M_1m_1$ is included in formula (XII) so as to show the presence or absence of a cation or an anion which required for the neutralization of an ion charge of the compound represented by the formula. Whether a dye is a cation or an anion or has a net ion charge depends on its auxochrome or substituent. The cation is typically an inorganic or organic ammonium ion or an alkali metal ion, and the anion may be either an inorganic anion or an organic anion and specific examples thereof include a halogen anion (e.g., fluorine ion, chlorine ion, bromine ion, iodine ion), a substituted arylsulfonic acid ion (e.g., p-toluenesulfonic acid ion, p-chlorobenzenesulfonic acid ion), an aryldisulfonic acid ion (e.g., 1,3-benzenesulfonic acid ion, 1,5-naphthalenedisulfonic acid ion, 2,6-naphthalenedisulfonic acid ion), an alkylsulfuric acid ion (e.g., methylsulfuric acid ion), a sulfuric acid ion, a thiocyanic acid ion, a perchloric acid ion, a tetrafluoroboric acid ion, a picric acid ion, an acetic acid ion and a trifluoromethanesulfonic acid ion.

Preferred are ammonium ion, an iodine ion, bromine ion and p-toluenesulfonic acid ion.

The nitrogen-containing heterocyclic ring represented by formula (VI), (VII), (VIII), (IX), (X), (XI) or (XII) is each substituted by at least one $(Q)_{k2}$—(Hy). The position to substitute is $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{24}$, $R_{25}$, $R_{26}$, $Y_1$, $L_3$ or $Z_7$.

Q represents a divalent linking group composed of an atom or an atomic group containing at least one of a nitrogen atom, a sulfur atom and an oxygen atom.

Q more preferably represents a divalent linking group having 20 or less carbon atoms and composed of a combination of one or more of an alkylene group (e.g., methylene, ethylene, propylene, butylene, pentylene), an arylene group (e.g., phenylene, naphthylene), an alkenylene group (e.g., ethenylene, propenylene), an amide group, an ester group, a sulfoamide group, a sulfonic acid ester group, a ureido group, a sulfonyl group, a sulfinyl group, a thioether group, an ether group, a carbonyl group, —N($R^1$)—(wherein $R^1$ represents a hydrogen atom, a substituted or unsubstituted alkyl group or a substituted or unsubstituted aryl group) and a heterocyclic divalent group (e.g., 6-chloro-1,3,5-triazine-2,4-diyl, pyrimidine-2,4-diyl, quinoxaline-2,3-diyl). More preferred are an ester group and an amide group.

k1 and k3 each is preferably 1 or 2.

More preferably, k1, k2 and k3 each is 1.

Typical examples of the compounds of the present invention are set forth below, but the present invention is not limited to these.

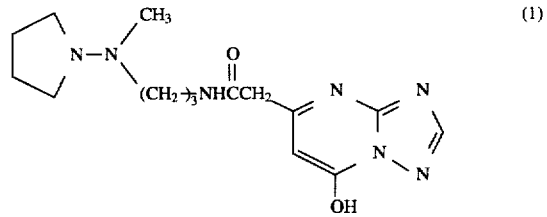

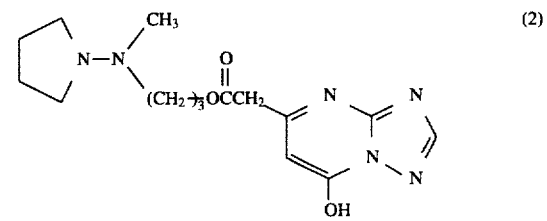

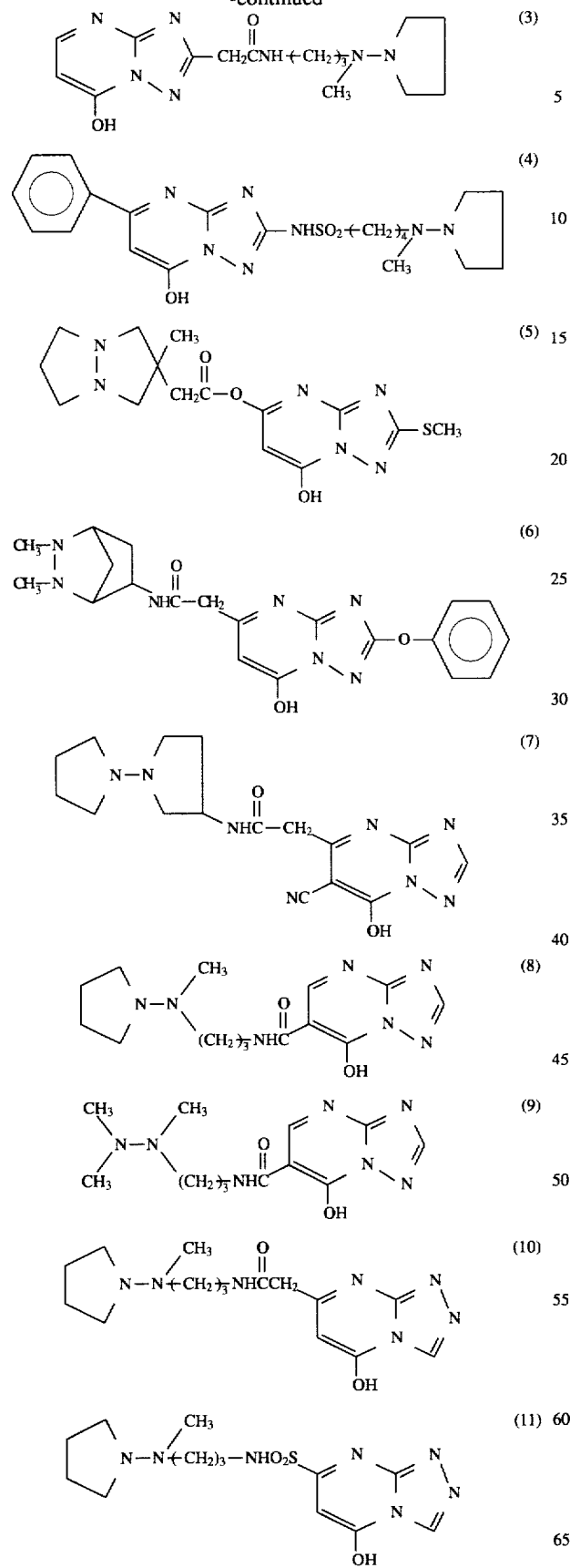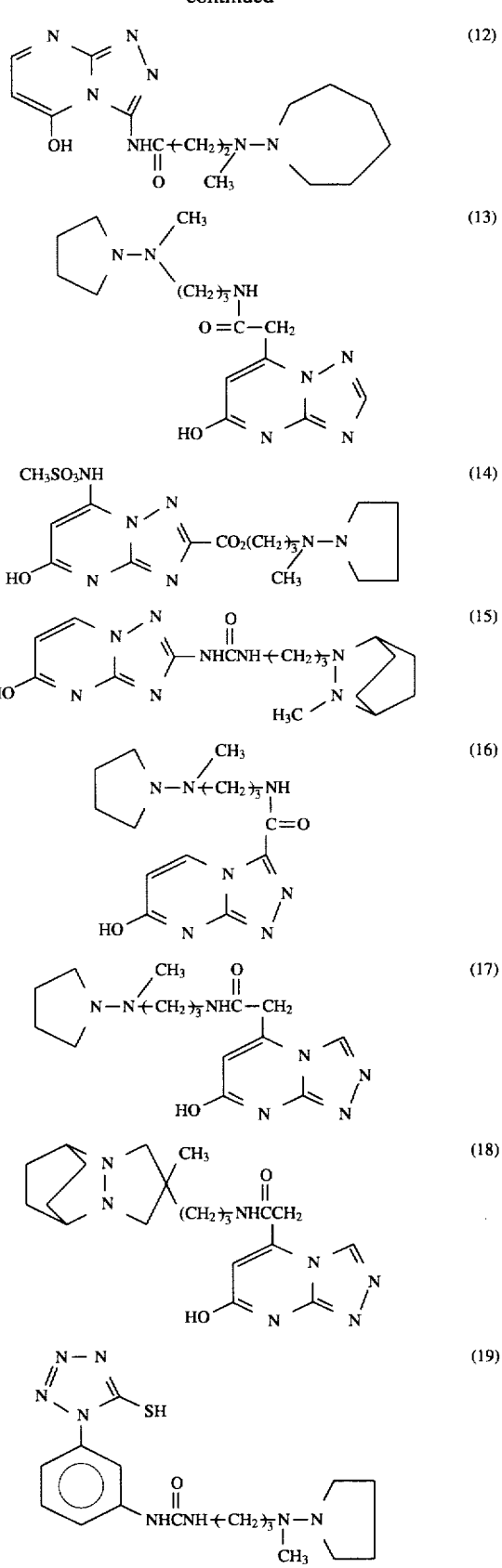

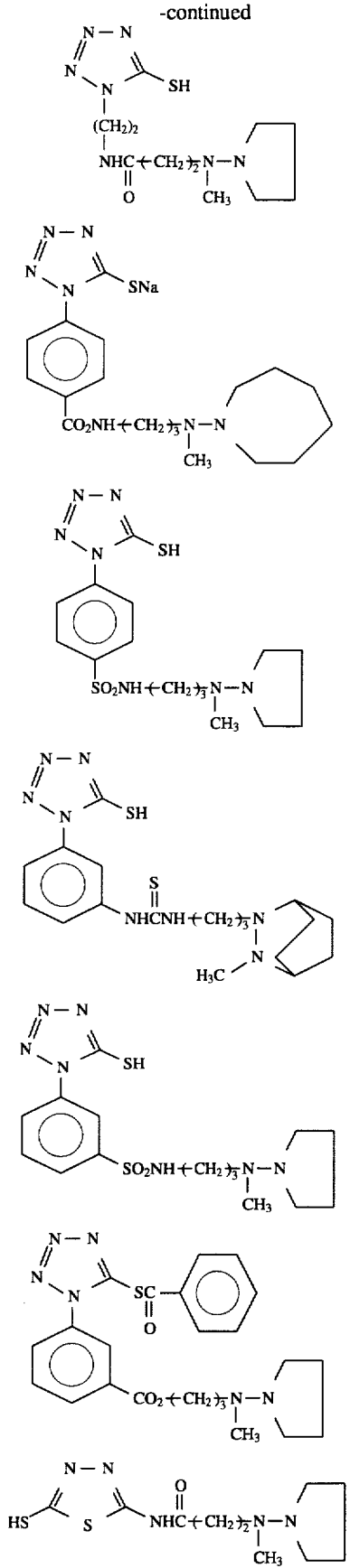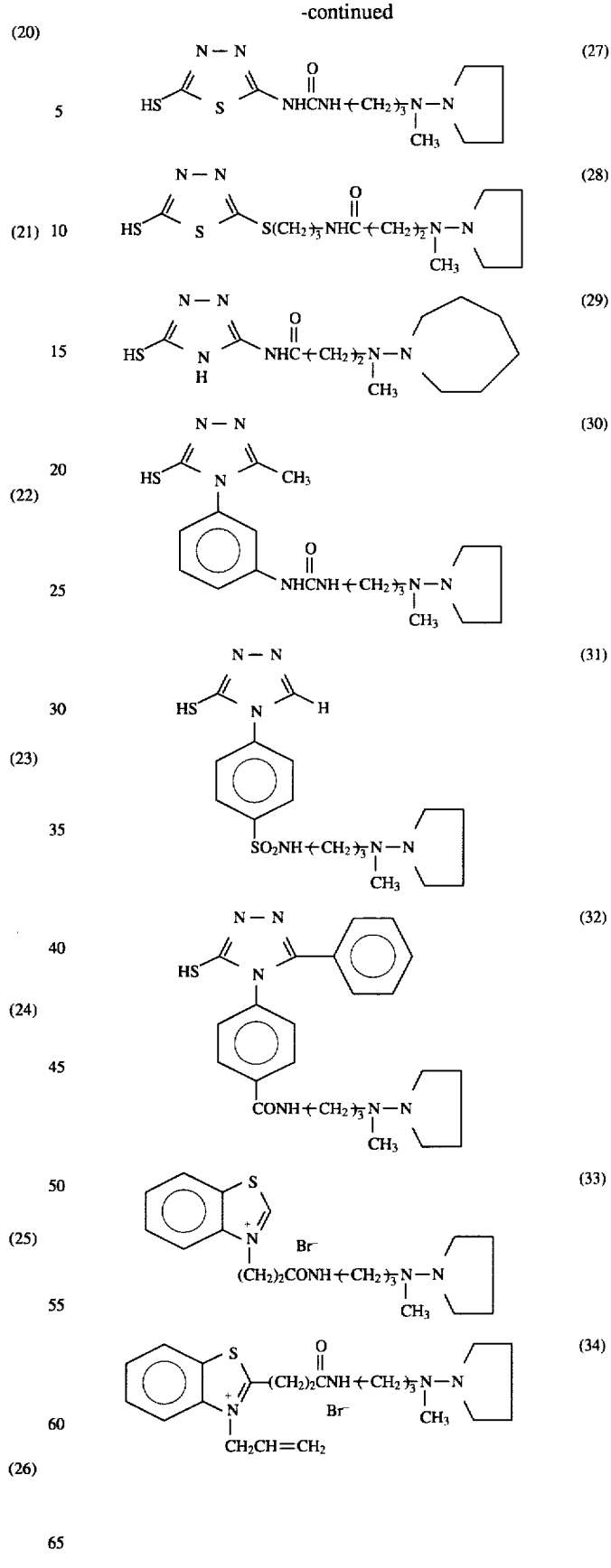

Of them, Compound (19) is preferred.

The compound represented by Het in formula (I) used in the present invention is described in U.S. Pat. No. 3,266,897, Belgian Patent 671,402, JP-A-60-138548, JP-A-59-68732, JP-A-59-123838, JP-B-58-9939 (the term "JP-B" as used herein means an "examined Japanese patent publication"), JP-A-59-137951, JP-A-57-202531, JP-A-57-164734, JP-A-57-14836, JP-A-57-116340, U.S. Pat. No. 4,418,140, JP-A-58-95728, JP-A-55-79436, OLS 2,205,029, OLS 1,962,605, JP-A-55-59463, JP-B-48-18257, JP-B-53-28084, JP-A-53-48723, JP-B-59-52414, JP-A-58-217928, JP-B-49-8334, U.S. Pat. Nos. 3,598,602 and 887,009, British Patent 965,047, Belgian Patent 737,809, U.S. Pat. No. 3,622,340, JP-A-60-87322, JP-A-57-211142, JP-A-58-158631, JP-A-59-15240, U.S. Pat. No. 3,671,255, JP-B-48-34166, JP-B-48-322112, JP-A-58-221839, JP-B-48-32367, JP-A-60-130731, JP-A-60-122936, JP-A-60-117240, U.S. Pat. No. 3,228,770, JP-B-43-13496, JP-B-43-10256, JP-B-47-8725, JP-B-47-30206, JP-B-47-4417, JP-B-51-25340, British Patent 1,165,075, U.S. Pat. Nos. 3,512,982 and 1,472,845, JP-B-39-22067, JP-B-39-22068, U.S. Pat. Nos 3,148,067, 3,759,901 and 3,909,268, JP-B-50-40665, JP-B-39-2829, U.S. Pat. No. 3,148,066, JP-B-45-22190, U.S. Pat. No. 1,399,449, British Patent 1,287,284, U.S. Pat. Nos. 3,900,32, 3,655,391 and 3,910,792, British Patent 1,064,805, U.S. Pat. Nos. 3,544,336 and 4,003,746, British Patents 1,344,525 and 972,211, JP-B-43-4136, U.S. Pat. No. 3,140,178, French Patent 2,015,456, U.S. Pat. No. 3,114,637, Belgian Patent 681,359, U.S. Pat. No. 3,220,839, British Patent 1,290,868, U.S. Pat. Nos. 3,137,578, 3,420,670, 2,759,908 and 3,622,340, OLS 2,501,261, DAS 1,772,424, U.S. Pat. No. 3,157,509, French Patent 1,351,234, U.S. Pat. No. 3,630,745, French Patent 2,005,204, German Patent 1,447, 796, U.S. Pat. No. 3,915,710, JP-B-49-8334, British Patents 1,021,199 and 919,061, JP-B-46-17513, U.S. Pat. No. 3,202, 512, OLS 2,553,127, JP-A-50-104927, French Patent 1,467, 510, U.S. Pat. Nos. 3,449,126, 3,503,936 and 3,576,638, French Patent 2,093,209, British Patent 1,246,311, U.S. Pat. Nos. 3,844,788 and 3,535,115, British Patent 1,161,264, U.S. Pat. Nos. 3,841,878 and 3,615,616, JP-A-48-39039, British Pat. 1,249,077, JP-B-48-34166, U.S. Pat. No. 3,671, 255, British Patent 1,459,160, JP-A-50-6323, British Patent 1,402,819, OLS 2,031,314, Research Disclosure No. 13651, U.S. Pat. Nos. 3,910,791, 3,954,478 and 3,813,249, British Patent 1,387,654, JP-A-57-135945, JP-A-57-96331, JP-A-57-22234, JP-A-59-26731, OLS 2,217,153, British Patents 1,394,371, 1,308,777, 1,389,089 and 1,347,544, German Patent 1,107,508, U.S. Pat. No. 3,386,831, British Patent 1,129,623, JP-A-49-14120, JP-B-46-34675, JP-A-50-43923, U.S. Pat. No. 3,642,481, British Patent 1,269,268, U.S. Pat. Nos. 3,128,185, 3,295,981, 3,396,023 and 2,895, 827, JP-B-48-38418, JP-A-48-47335, JP-A-50-87028, U.S. Pat. Nos. 3,236,652 and 3,443,951, British Patent 1,065,669, U.S. Pat. Nos. 3,312,552, 3,310,405 and 3,300,312, British Patents 952,162, 952,162 and 948,442, JP-A-49-120628, JP-B-48-35372, JP-B-47-5315, JP-B-39-18706, JP-B-43-4941 and JP-A-59-34530, and can be synthesized according to these publications.

The compound represented by Hy in formula (I) of the present invention can be synthesized according to various methods, for example, by the alkylation of hydrazine. Known examples of the alkylation include a direct alkylation using an alkyl halide and an alkyl sulfonate, a reductive alkylation using a carbonyl compound and sodium hydrogenated cyanoborate and an acylation followed by reduction using a hydrogenated lithium aluminum. The compound of Hy can be synthesized by referring to the disclosure, for example, in S. R. Sandler and W. Karo, "Organic Functional Group Preparation", Vol. 1, Chap. 14, pp. 434–465 (1968) published by Academic Press, and E. L. Clennan, *Journal of the American Chemical Society*, Vol. 112, No. 13, p. 5080 (1990).

The bond-forming reaction including the amide bond-forming or ester bond-forming reaction in the moiety —$(Q)_{k2}$—(Hy) can be conducted utilizing methods known in the field of the organic chemistry. Namely, any of a method of connecting Het to Hy, a method of connecting Hy to a synthesis starting material and an intermediate of Het and then synthesizing Het, and reversely, a method of connecting a synthesis starting material and an intermediate of Hy to the Het moiety and then synthesizing Hy can used and these can be appropriately selected in the synthesis. With respect to he synthesis reaction for connecting these compounds, many publications concerning the organic synthesis reaction, for example, *Shin-Jikken Kagaku Koza* 14 "*Yuki-Kagobutsu no Gosei to Hanno*" compiled by Nippon Kagaku-kai, Vols. I to V, Maruzen, Tokyo (1977), Yoshio Ogata, *Yuki Hanno Ron*, Maruzen, Tokyo (1962), L. F. Fieser and M. Fieser, *Advanced Organic Chemistry*, Maruzen, Tokyo (1962) can be referred to.

Specific synthesis examples are provided in Examples 1 and 2.

In the present invention, a spectral sensitizing dye is preferably used. For example, any of conventionally known dyes such as a cyanine dye, a merocyanine dye, a rhodacyanine dye, an oxonol dye, a hemicyanine dye, a benzylidene dye, a xanthene dye and a styryl dye can be used. Examples thereof include dyes described in T. H. James, *The Theory of the Photographic Process*, 3rd version, pp. 198–228 (1966), Macmillan.

More preferred are dyes described in JP-A-5-216152 and represented by formula (XI), (XII), (XIII) and (XIV) therein, with the dyes set forth as specific examples thereof being particularly preferred.

The compound represented by formula (I) of the present invention and the sensitizing dye used in the present invention are incorporated into the silver halide emulsion of the present invention by dispersing them directly in the emulsion or by dissolving them in a sole or mixed solvent of water, methanol, ethanol, propanol, acetone, methylcellosolve, 2,2,3,3-tetrafluoropropanol, 2,2,2-trifluoroethanol, 3-methoxy-1-propanol, 3-methoxy-1-butanol, 1-methoxy-2-propanol, N,N-dimethylformamide and then adding the solution to the emulsion.

Also, a method in which a dye and the like are dissolved in a volatile organic solvent, the resulting solution is dispersed in water or a hydrophilic colloid, and then the dispersion is added to the emulsion as described in U.S. Pat. No. 3,469,987, a method in which a water-insoluble dye and the like are dispersed in a water-soluble solvent without being dissolved and the dispersion is added to the emulsion as described in JP-A-46-24185, a method in which a dye is dissolved in an acid and the solution is added to the emulsion or converted to an aqueous solution with an acid or a base being present together and then added to the emulsion as described in JP-B-44-23389, JP-B-44-27555 and JP-B-57-22091, a method in which an aqueous solution or a colloidal dispersion is first prepared with a surfactant being present together and then added to the emulsion as described in U.S. Pat. Nos. 3,822,135 and 4,006,026, a method in which the dye and the like are dispersed directly in a hydrophilic colloid and the dispersion is added to the emulsion as described in JP-A-53-102733 and JP-A-58-105141, or a method in which a dye is dissolved using a compound capable of redox and the solution is added to the emulsion as described in JP-A-51-74624 can be used.

An ultrasonic can also be used in the dissolution.

The sensitizing dye and the compound represented by formula (I) for use in the present invention may be added to the silver halide emulsion of the present invention at any step known as useful during the preparation of emulsion. For example, they may be added at any time or step prior to the coating of emulsion such as before the grain formation and/or desalting of silver halide or during desalting and/or between after desalting and before the initiation of chemical ripening as disclosed in U.S. Pat. Nos. 2,735,766, 3,628,960, 4,183,756 and 4,225,666, JP-A-58-184142 and JP-A-60-196749, or immediately before or during chemical ripening or after chemical ripening but prior to coating as disclosed in JP-A-58-113920. Further, the compound used solely or in combination with a compound having a different structure may be added by sharing the addition time, for example, between during the grain formation and during chemical ripening or after the completion of chemical ripening or between before or during chemical ripening and after the completion thereof, or may be added by varying the kind of the compound to be added dividedly or of the combination of compounds, as disclosed in U.S. Pat. No. 4,225,666 and JP-A-58-7629.

The addition amount of the sensitizing dye used in the present invention varies depending upon the shape and the size of silver halide but it is preferably from $4 \times 10^{-8}$ to $8 \times 10^{-2}$ mol per mol of silver halide.

The compound represented by formula (I) of the present invention may be added either before or after the addition of the sensitizing dye and it is preferably present in a silver halide emulsion in an amount of from $1\times10^{-9}$ to $5\times10^{-1}$ mol, more preferably from $1\times10^{-8}$ to $2\times10^{-2}$ mol, per mol of silver halide.

The ratio (molar ratio) of the sensitizing dye to the compound represented by formula (I) may be any value but it is advantageous that the ratio of the sensitizing dye to the compound of formula (I) is in the range between 1,000/1 and 1/1,000, particularly preferably between 100/1 and 1/10.

The silver halide used in the present invention may be any of silver chloride, silver bromide, silver iodide, silver chlorobromide, silver chloroiodide, silver chloroiodobromide and silver iodobromide. The silver halide emulsion used in the present invention may contain these silver halide grains individually or as a mixture of a plurality of these grains. The silver halide grain may have different phases between the inside and the surface layer, may have a multiphase structure containing a junction structure, may have a local phase on the grain surface or may have a uniform phase throughout the grain. The grains having different phase patterns may be present together.

The silver halide grain used in the present invention may be either monodisperse or polydisperse and may have a regular crystal form such as cubic, octahedral or tetradecahedral, an irregular crystal form, or a composite form of these crystal forms. A tabular emulsion, in which AgX grains having an aspect ratio (the ratio of circle-corresponding diameter of silver halide grain to the grain thickness) of 3 or more account for 50% or more of the total projected area of the grains, may also be used. The aspect ratio is more preferably 5 or more, or 8 or more. Also, an emulsin composed of a mixture of these diversified crystal forms may be used. These various kinds of emulsions may be either of a surface latent image type forming a latent image mainly on the surface or of an internal latent image type forming it inside the grain.

The photographic emulsion used in the present invention can be prepared according to the methods described in P. Glafkides, *Chemie et Physique Photographigue*, Paul Montel (1967), G. F. Daffin, *Photographic Emulsion Chemistry*, Focal Press (1966), V. L. Zelikman et al., *Making and Coating Photographic Emulsion*, Focal Press (1964), F. H. Claes et al., *The Journal of Photographic Science*, (21)39–50 (1973), F. H. Claes et al., *The Journal of Photographic Science*, (21)85–92 (1973), JP-B-55-42737, U.S. Pat. Nos. 4,400,463 and 4,801,523, JP-A-62-218959, JP-A-63-213836, JP-A-63-218938, and Japanese Patent Application No. 62-291487. That is, the emulsion can be prepared by any of an acid process, a neutral process and an ammonia process and the reaction of a soluble silver salt with a soluble halogen salt may be conducted by a single jet process, a double jet process or a combination thereof. A method of forming grains in the presence of excess silver (a so-called reverse mixing method) may also be used. Further, as one figure of the double jetting process, a method comprising keeping constant the pAg of a liquid phase in which silver halide is formed, a so-called controlled double jet process, may also be used. According to this method, the silver halide emulsion obtained can have a regular crystal form and a nearly uniform grain size.

Further, an emulsion prepared by a so-called conversion process which comprises a step for converting the silver halide which has already been formed until the completion of silver halide grain formation or an emulsion subjected to the same halogen conversion after the completion of silver halide grain formation can also be used.

In the preparation of silver halide grains of the present invention, a silver halide solvent may be used.

Examples of silver halide solvents in frequent use include thioether compounds (for example, those described in U.S. Pat. Nos. 3,271,157, 3,574,628, 3,704,130 and 4,276,347), thione compounds and thiourea compounds (for example, those described in JP-A-53-144319, JP-A-53-82408, JP-A-55-77737) and amine compounds (for example, those described in JP-A-54-100717) and these can be used in the present invention. Also, ammonia may be used in the range of causing no adverse effect.

In the preparation of silver halide grains of the present invention, a method of increasing the addition rate, addition amount and addition concentration of a silver salt solution (e.g., an aqueous silver nitrate solution) and a halide solution (e.g., an aqueous sodium chloride solution) as the time passing is preferably used so as to accelerate the growth of grains. With respect to this method, for example, British Patent 1,335,925, U.S. Pat. Nos. 3,672,900, 3,650,757 and 4,242,445, JP-A-55-142329, JP-A-55-158124, JP-A-55-113927, JP-A-58-113928, JP-A-58-111934 and JP-A-58-111936 may be referred to.

During the silver halide grain formation or physical ripening thereof, cadmium salt, zinc salt, lead salt, potassium salt, rhenium salt, lutenium salt, iridium salt or its complex salt, rhodium salt or its complex salt, or iron salt or its complex salt may be present together. In particular, rhenium salt, iridium salt, rhodium salt and iron salt are more preferred.

The addition amount thereof may be freely varied depending upon the need and, for example, with respect to the iridium salt (e.g., $Na_3IrCl_6$, $Na_2IrCl_6$, $Na_3Ir(CN)_6$), it is preferably in the range of from $1\times10^{-8}$ to $1\times10^{-5}$ per mol of silver and with respect to the rhodium salt (e.g., $RhCl_3$, $K_3Rh(CN)_6$), it is in the range of from $1\times10^{-8}$ to $1\times10^{-6}$ per mol of silver.

The silver halide emulsion of the present invention may be used without being chemically sensitized but may be subjected to chemical sensitization, if desired.

The chemical sensitization can be carried out by a so-called gold sensitization using a gold compound (for example, as in U.S. Pat. Nos. 2,448,060 and 3,320,069), a sensitization using a metal such as iridium, platinum, rhodium and palladium (for example, as in U.S. Pat. Nos. 2,448,060, 2,566,245 and 2,566,263), a sulfur sensitization using a sulfur-containing compound (for example, as in U.S. Pat. No. 2,222,264), a selenium sensitization using a selenium compound, a reduction sensitization using tin salts, thiourea dioxide or polyamide (for example, as in U.S. Pat. Nos. 2,487,850, 2,518,698 and 2,521,925), or a combination of two or more of these sensitizations.

The silver halide emulsion of the present invention is preferably sensitized by a gold sensitization, a sulfur sensitization or a combination thereof. The gold sensitizer and the sulfur sensitizer each is preferably added in an amount of from $1\times10^{-7}$ to $1\times10^{-2}$ mol, more preferably from $5\times10^{-6}$ to $1\times10^{-3}$ mol, per mol of silver. In the case of a combination of a gold sensitization and a sulfur sensitization, the molar ratio of the gold sensitizer to the sulfur sensitizer is preferably between 1:3 and 3:1, more preferably between 1:2 and 2:1.

The temperature at the chemical sensitization in the present invention can be freely selected from temperatures between 30° C. and 90° C. The pH at the chemical sensitization is preferably from 4.5 to 9.0, preferably from 5.0 to 7.0. The time for the chemical sensitization cannot be generally determined because it varies according to the temperature, the kind and amount of chemical sensitizer used and the pH, but it can be freely selected from the range between several minutes and several hours and it is usually from 10 minutes to 200 minutes.

The sensitizing dye used in the present invention is often used in combination with water-soluble iodide salt such as potassium iodide, water-soluble bromide salt such as potassium bromide or water-soluble thiocyanate such as potassium thiocyanate so as to enhance the adsorption of the dye to silver halide or J-aggregate formation, and this is preferably adopted in the present invention. The water-soluble bromide salt or the water-soluble thiocyanate provides remarkable effects in this respect in the case of silver chloride or silver chlorobromide having a large silver chloride content.

For the purpose of achieving an ultrahigh speed processing in which the development time is reduced to 30 seconds or less, a high silver chloride emulsion having a silver chloride content of 50 mol % or more is preferred. From the standpoint of this object, since the iodine ion has strong development inhibiting property as well known, the iodine ion inclusive of the above-described water-soluble iodide salt is preferably reduced to 0.05 mol % or less per mol of silver.

In producing a silver halide photographic material suitable for the ultrahigh speed processing, a high silver chloride emulsion having a silver chloride content of 80 mol % or more is more preferred and, if the above-described water-soluble bromide salt and/or water-soluble thiocyanate are used in combination with such an emulsion, J-aggregate formation is enhanced and higher spectral sensitivity is advantageously obtained, but the addition amount thereof is preferably suppressed to the range of from 0.03 to 3 mol %, particularly from 0.08 to 1 mol %, per mol of silver.

The high silver chloride grain having a silver chloride content of 80 mol % or more preferably has a localized phase in the grain, as disclosed in JP-A-2-248945, which has such a property as that when it is spectrally sensitized in an infrared region, a high sensitivity and an excellent stability, particularly stability of a latent image, can be obtained. As described in the above-cited patent application, the localized phase preferably has a silver bromide content of more than 15 mol %, more preferably from 20 to 60 mol % and most preferably from 30 to 50 mol %, with the rest being silver chloride. The localized phase may be present inside, on the surface, or on the subsurface of the silver halide grain, or the inside may be divided into two portions by the surface or the subsurface. The localized phase present in the inside or on the surface may have a stratiform structure enclosing the silver halide grain or a discontinuous and independent structure. Specifically, the localized phase having a silver bromide content higher than that in the periphery is preferably established such that a localized phase having a silver bromide content exceeding at least 15 mol% is locally and epitaxially grown on the surface of silver halide grain.

The silver bromide content of the localized phase can be determined by the analysis according to X-ray diffraction method (as described, for example, in *Shin-Jikken Kagaku Koza* 6, *Kozo Kaiseki*, compiled by Nippon Kagaku-kai, Maruzen) or an XPS method (as described, for example, in *Hyomen-Bunseki, IMA, Auger Denshi.Kodensihi Bunnko no Oyo*, Kodansha). The localized phase is preferably composed of from 0.1 to 20% of silver, more preferably from 0.5 to 7% of silver, based on the entire amount of silver constituting the silver halide grain.

The interface between the localized phase having a high silver bromide content and other phases may be clearly bounded or may be a narrow transition region where the halogen composition gradually changes.

The localized phase having a high silver bromide content can be formed by various methods. For example, the localized phase can be formed by the reaction of a soluble silver salt with a soluble halogen salt using a single jet process or a double jet process. Also, the localized phase can be formed by a so-called conversion method comprising a step for converting silver halide which has already been formed into silver halide having a small solubility product. Or, the localized phase can also be formed by adding a silver bromide fine grain to recrystallize it on the surface of a silver chloride grain.

The silver halide emulsion prepared according to the present invention can be used for either a color photographic material or a black-and-white photographic material.

The silver halide emulsion of the present invention may have any known silver halide composition, crystal phase or size. Preferred examples thereof are described in JP-A-2-269334, from line 17 in the right upper column of page 19 to line 7 in the right upper column of page 20.

Examples of the color photographic material include, in particular, color paper, film for color photographing and color reversal film, and examples of the black-and-white photographic material include X-ray film, film for general photographing and film for printing light-sensitive material.

The additives for the photographic material to which the emulsion of the present invention is applied are not particularly restricted and, for example, *Research Disclosure*, Vol. 176, Item 17643 (RD17643) and *ibid.*, Vol. 187, Item 18716 (RD18716) may be referred to thereon.

The portions in RD17643 and RD18716 including the description about various additives are listed in Table 1 below.

TABLE 1

| | Kinds of Additives | RD17643 | RD18716 |
|---|---|---|---|
| 1 | Chemical sensitizer | p. 23 | p. 648, right column |
| 2 | Sensitivity increasing agent | | p. 648, right column |
| 3 | Spectral sensitizer, supersensitizer | pp. 23–24 | p. 648, right column-p.649, right column |
| 4 | Whitening agent | p.24 | |
| 5 | Antifoggant and stabilizer | pp. 24–25 | p. 649, right column |
| 6 | Light absorbent, filter dye, UV absorbent | pp. 25–26 | p. 649, right column-p.650, left column |
| 7 | Stain inhibitor | p. 25, right column | p. 650, from left to right columns |
| 8 | Dye image stabilizer | p. 25 | |
| 9 | Hardening agent | p. 26 | p. 651, left column |
| 10 | Binder | p. 26 | p. 651, left column |
| 11 | Plasticizer, lubricant | p. 27 | p. 650, right column |
| 12 | Coating aid, surfactant | pp. 26–27 | p. 650, right column |
| 13 | Antistatic agent | p. 27 | p. 650, right column |

The dye will be described in more detail.

In the light-sensitive material of the present invention, a colloid silver or a dye is used for preventing irradiation, for preventing halation, and in particular, for ensuring separation in the spectral sensitivity distribution of respective light-sensitive layers as well as safety to safelight.

Examples of such a dye include oxonol dyes having a pyrazolone nucleus, a barbituric nucleus or a barbituric acid nucleus described in U.S. Pat. Nos. 506,385, 1,177,429, 1,131,884, 1,338,799, 1,385,371, 1,467,214, 1,438,102 and 1,553,516, JP-A-48-85130, JP-A-49-114420, JP-A-52-117123, JP-A- 55-161233, JP-A-59-111640, JP-B-39-22069, JP-B-43-13168, JP-B-62-273527 and U.S. Pat. Nos. 3,247,127, 3,469,985 and 4,078,933, other oxonol dyes described in U.S. Pat. Nos. 2,533,472 and 3,379,533, British Patent 1,278,621, JP-A-1-134447 and JP-A-1-183652, azo dyes described in British Patents 575,691, 680,631, 599,623, 786,907, 907,125 and 1,045,609, U.S. Pat. No. 4,255,326 and JP-A-59-211043, azomethine dyes described in JP-A-50-100116, JP-A-54-118247, British Patent 2,014,598 and 750,031, anthraquinone dyes described in U.S. Pat. No. 2,865,752, arylidene dyes described in U.S. Pat. Nos. 2,538,009, 2,688,541 and 2,538,008, British Patents 584,609 and 1,210,252, JP-A-50-40625, JP-A-51-3623, JP-A-51-10927, JP-A-54-118247, JP-B-48-3286 and JP-B-59-37303, styryl dyes described in JP-B-28-3082, JP-B-44-16594 and JP-B-59-28898, triarylmethane dyes described in British Patents 446,538 and 1,335,422 and JP-A-59-228250, merocyanine dyes described in British Patents 1,075,653, 1,153,341, 1,284,730, 1,475,228 and 1,542,807, and cyanine dyes described in U.S. Pat. Nos. 2,843,486 and 3,294,539 and JP-A-1-291247.

These dyes are prevented from diffusing by the following methods. For example, a ballast group is incorporated into the dye to render the dye non-diffusible.

Also, for example, U.S. Pat. Nos. 2,548,564, 4,124,386 and 3,625,694 disclose a method for localizing a dye in a specific layer by the interaction between a dye molecule and a hydrophilic polymer which is made present together in the layer as a mordant and has a charge counter to the dissociated anionic dye.

Further, JP-A-56-12639, JP-A-55-155350, JP-A-55-155351, JP-A-63-27838, JP-A-63-197943 and European Patent 15601 disclose a method of dyeing a specific layer by using a water-insoluble dye solid.

Furthermore, U.S. Pat. Nos. 2,719,088, 2,496,841 and 2,496,843 and JP-A-60-45237 disclose a method of dyeing a specific layer by using a metal salt fine particles to which a dye is adsorbed.

Among the above-described additives, preferred examples of the antifoggant and stabilizer include azoles {for example, benzothiazolium salts, nitroimidazoles, nitrobenzimidazoles, chlorobenzimidazoles, bromobenzimidazoles, nitroindazoles, benzotriazoles, aminotriazoles}; mercapto compounds {for example, mercaptothiazoles, mercaptobenzothiazoles, mercaptobenzimidazoles, mercaptothiadiazoles, mercaptotetrazoles (in particularly, 1-phenyl-5-mercaptotetrazole), mercaptopyrimidines, mercaptotriazines}; thioketo compounds such as oxzaolinethione; azaindenes {for example, triazaindenes, tetraazaindenes (in particular, 4-hydroxysubstituted (1,3,3a,7)tetraazaindenes), pentaazaindenes}; benzenethiosulfonic acid, benzenesulfinic acid and benzenesulfonic acid amide.

The color coupler is preferably nondiffusible as having a hydrophobic group called a ballast group in the molecule or is polymerized. The coupler may be either four equivalent or two equivalent to a silver ion. Also, a colored coupler providing an effect of correcting color or a coupler which releases a development inhibitor upon development (so-called DIR coupler) may be added. A non-color-forming DIR coupling compound which provides a colorless product upon coupling and releases a development inhibitor may also be added.

Preferred examples of these are described in JP-A-62-215272, from line 4 in the right upper column of page 91 to line 6 in the left upper column of page 121 and JP-A-2-33144, from line 14 in the right upper column of page 3 to the bottom line in the left upper column of page 18 and from line 6 in the right upper column of page 30 to line 11 in the right lower column of page 35.

Examples of the magenta coupler include 5-pyrazolone couplers, pyrazolobenzimidazole couplers, pyrazolotriazole couplers, pyrazolotetrazole couplers, cyanoacetylcoumarone couplers and open-chained acylacetonitrile couplers, examples of the yellow coupler include acylacetamide couplers (e.g., benzoylacetanilides, pivaloylacetanilides), and examples of the cyan coupler include naphthol couplers and phenol couplers. As the cyan coupler, phenolic couplers having an ethyl group at the meta-position of the phenol nucleus, 2,5-diacylamino-substituted phenolic couplers, phenolic couplers having a phenylureido group at the 2-position and an acylamino group at the 5-position, and couplers having sulfonamide or amide substituted at the 5-position of the naphthol as described in U.S. Pat. Nos. 3,772,002, 2,772,162, 3,758,308, 4,126,396, 4,334,01.1, 4,327,173, 3,446,622, 4,333,999, 4,451,559 and 4,427,767 are preferred in view of excellent image fastness.

The above-described couplers may be incorporated to the same layer as a mixture of two or more thereof or different compounds can of course be added to different two or more layers.

Representative examples of the discoloration inhibitor include hydroquinones, 6-hydroxychromans, 5-hydroxycoumaranes, spirochromans, p-alkoxyphenols, hindered phenols including bisphenols, gallic acid derivatives, methylenedioxybenzenes, aminophenols, hindered amines and ether or ester derivatives obtained by silylating or alkylating the phenolic hydroxyl group of these compounds. Metal complexes represented by (bissalicylaldoximate) nickel complex and (bis-N,N-dialkyldithiocarbamate) nickel complex can also be used.

In the photographic processing of the light-sensitive material used in the present invention, any known method and any known processing solution may be used. The processing temperature is usually selected from between 18° C. and 50° C., but temperatures lower than 18° C. or temperatures higher than 50° C. may be used. According to the purpose, either development for forming a silver image (black-and-white photographic processing) or a color photographic processing comprising development for forming a color image can be applied.

The black-and-white developer can contain known developing agents such as dihydroxybenzenes (e.g., hydroquinone), 3-pyrazolidones (e.g., 1-phenyl-3-pyrazolidone) and aminophenols (e.g., N-methyl-p-aminophenol) individually or in combination.

The color developer generally comprises an alkaline aqueous solution containing a color developing agent. The color developing agent may be a known aromatic primary amine developing agent such as phenylenediamines (e.g., 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 3-methyl-4-amino-N-ethyl-N-β-methanesulfonamidoethylaniline, 4-amino-3-methyl-N-ethyl-N-β-methoxyethylaniline).

In addition, those described in F. A. Mason *Photographic Processing Chemistry*, Focal Press (1966), pp. 226–229, U.S. Pat. Nos. 2,193,015 and 2,592,364 and JP-A-48-64933 may also be used.

The developer may contain a pH buffer such as sulfite, carbonate, borate or phosphate of an alkali metal, or a development inhibitor or antifoggant such as bromide, iodide or an organic antifoggant. If desired, the developer may further contain a hard water softener, a preservative such as hydroxylamine, an organic solvent such as benzyl alcohol and diethylene glycol, a development inhibitor such as polyethylene glycol, tetrammonium salt and amines, a dye-forming coupler, a competitive coupler, a fogging agent such as sodium boron hydride, an auxiliary developing agent such as 1-phenyl-3-pyrazolidone, a tackyfying agent, a polycarboxylic acid-based chelating agent described in U.S. Pat. No. 4,083,723, or an antioxidant described in OLS 2,622,950.

In the color photographic processing, the photographic material is usually subjected to bleaching after color development. The bleaching may be conducted simultaneously with fixing or separately therefrom. As the bleaching agent, compounds of polyvalent metals such as iron(III), cobalt(III), chromium(V) or copper(II), peracids, quinones, or nitroso compounds are used. For example, ferricyanides, bichromates, organic complex salts of iron(III) or cobalt(III), complex salts of an aminopolycarboxylic acid such as ethylenediaminetetraacetate, nitrilotriacetate or 1,3-diamino-2-propanol tetraacetate or of an organic acid such as citric acid, tartaric acid or malic acid, persulfates, permanganates or nitrosophenols may be used. Among these, potassium ferricyanide, sodium ethylenediaminetetraacetate iron(III) and ammonium ethylenediaminetetraacetate iron(III) are particularly useful. A complex salt of ethylenediaminetetraacetate iron(III) is useful either in an independent bleaching solution or in a monobath bleach-fixing solution.

The bleaching or bleach-fixing solution may contain a bleaching accelerator described in U.S. Pat. Nos. 3,042,520 and 3,241,955, JP-B-45-8506 and JP-B-45-8836, a thiol compound described in JP-A-53-65732, and other various additives. After the bleaching or bleach-fixing, water washing may be applied or only stabilization may be conducted.

As the support for use in the present invention, a transparent film such as a cellulose nitrate film and a polyethylene terephthalate, which is usually used for the photographic material, or a reflection-type support can be used.

The term "reflective support" used in the present invention means one which increases reflectivity to make sharp a dye image formed in the silver halide emulsion layer, and the reflective support includes a support covered by a hydrophobic resin having dispersed therein a light-reflective substance such as titanium oxide, zinc oxide, calcium carbonate or calcium sulfate and a support made of a hydrophobic resin having dispersed therein light-reflective substance, so as to increase reflectance in a visible light wavelength region. Examples thereof include baryta paper, polyethylene-laminated paper, polypropylene-based synthetic paper and a transparent support provided with a reflection layer or using a reflective substance and specific examples thereof include glass plate, polyethylene terephthalate, polyester film such as cellulose triacetate or cellulose nitrate, polyamide film, polycarbonate film, polystyrene film and vinyl chloride resin. These supports can be appropriately selected according to the use object.

The exposure for achieving a photographic image can be carried out by a conventional method. Stated more specifically, any of various known light sources such as natural light (sunlight), a tungsten lamp, a fluorescent lamp, a mercury lamp, a xenon arc lamp, a carbon arc lamp, a xenon flash lamp, a laser, LED or CRT can be used. The exposure time may of course be in the range between 1/1,000 second and 1 second which is an ordinary exposure time for a camera and moreover, it may be shorter than 1/1,000 second, for example, in the range between $1/10^4$ second and $1/10^6$ second with the use of a xenon flash lamp, or may be longer than 1 second. The spectral composition of the light may be controlled with a color filter, if desired. The exposure may be also carried out with laser beams. Further, the exposure may be carried out with light emitted from a phosphor excited from electron beams, X rays, γ rays or α rays.

The present invention will be described below in greater detail with reference to the Examples set forth below, but the present invention is not limited to these.

EXAMPLE 1

Synthesis of compound (1):
Compound (1) is synthesized according to Scheme 1.

Scheme 1:

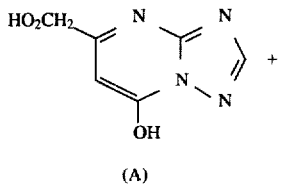

(A)

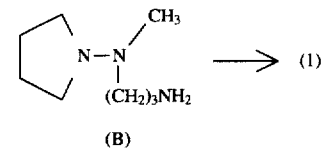

(B)

3.6 g (0.017 mol) of dicyclohexylcarbodiimide (DCC) was added to a mixture of 3.4 g (0.017 mol) of compound (A), 3 g (0.019 mol) of compound (B) and 25 ml of dimethylformamide and heated with stirring at an external temperature of 45° C. for 3 hours. After leaving the mixture overnight, the precipitated crystal was removed by filtration and the solvent in the filtrate was distilled off under reduced pressure. Ethanol was added to the harz-like (rosin-like) residue and after dissolving it therein, the mixture was crystallized with the addition of ethyl acetate. This procedure was repeated five times and the resulting colorless crystal was separated by suction filtration and dried. Yield by volume: 1.74 g (yield: 30%, melting point: 95°–97° C.).

EXAMPLE 2

Synthesis of Compound (19)
Compound (19) was synthesized according to Scheme 2.

Scheme 2:

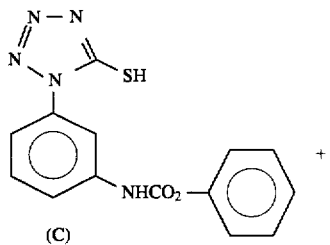

(C)

Scheme 2:

-continued

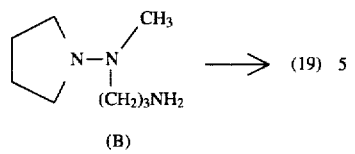

2.8 g (0.018 mol) of Compound (B) was added to a mixture of 5 g (0.016 mol) of Compound (C), 2.9 g (0.035 mol) of 2-methylimidazole and 50 ml of acetonitrile, and heated with reflux under a nitrogen stream for 30 minutes. After cooling it, the precipitated crystal was separated by suction filtration and washed by boiling for 30 minutes with the addition of 100 ml of methanol. After leaving it to cool, 4 g of colorless crystal was obtained by suction filtration (yield: 60%, melting point: 196°–198° C.).

EXAMPLE 3

1,000 ml of water, 25 g of deionized bone gelatin, 15 ml of a 50% $NH_4NO_3$ aqueous solution and 7.5 ml of a 25% $NH_3$ aqueous solution were poured into a reaction vessel and kept at 50° C. to dry well the mixture, and then thereto 750 ml of an aqueous solution of 1N-$AgNo_3$ and an aqueous solution of 1N-KBr were added over 50 minutes. The silver potential was kept at +50 mV for the saturated calomel electrode during the reaction.

The resulting silver bromide grains each was cubic and a monodisperse grain having a side length on average falling within the range of from 0.75 to 0.8 μm. To this emulsion, an isobutene-monosodium maleate copolymer was added, the emulsion was water-washed by sedimentation to desalt the emulsion, 95 g of deionized bone gelatin and 430 ml of water were added thereto, the pH and pAg were adjusted at 50° C. to 6.5 and 8.3, respectively, and this emulsion was ripened at 55° C. for 50 minutes with the addition of sodium thiosulfate so as to have an optimum sensitivity. The resulting emulsion had a silver bromide content of 0.74 mol/kg.

Further, to 45 g of this emulsion, sensitizing dyes and subsequently compounds represented by formula (I) were added as shown in Table 2 below, followed by mixing with stirring at 40° C.

Furthermore, to each of the resulting mixtures, 15 g of 10% gel of gelatin and 55 ml of water were added and then each solution was coated on a polyethylene terephthalate film base in such a manner as described below.

The coated amount was adjusted to give silver coverage of 2.5 $g/m^2$ and gelatin coverage of 3.8 $g/m^2$. On the upper layer, an aqueous solution mainly comprising 0.22 g/l of sodium dodecylbenzenesulfonate, 0.50 g/l of sodium p-sulfostyrene homopolymer, 3.1 g/l of sodium 2,4-dichloro-6-hydroxy-1,3,5-triazine and 50 g/l of gelatin was coated simultaneously, to give gelatin coverage of 1.0 $g/m^2$.

Each of these samples was exposed to tungsten light (2856° K.) for 1 second through a continuous wedge using a blue filter (a band pass filter capable of transmitting light between 395 nm and 440 nm) and a yellow filter (a filter capable of transmitting light having a wavelength longer than 560 nm).

After the exposure, each sample was developed with a developer having the following composition at 20° C. for 10 minutes. The developed films were subjected to density measurement using a densitometer manufactured by Fuji Photo Film Co., Ltd. and a yellow filter sensitivity (SY), a blue filter sensitivity (SB) and fog were determined on each sample. The standard point of the optical density in determining sensitivities was [fog+0.2]. SB are shown in terms of a relative sensitivity taking the sensitivity of a sample in which neither sensitizing dye nor hydrazine compound was added as 100 (standard) and SY are shown by a relative value among samples in which the same sensitizing dye was added taking the sensitivity of a sample free of a hydrazine compound as 100.

[Composition of Developer]

| | |
|---|---|
| Metol | 2.5 g |
| α-Ascorbic acid | 10.0 g |
| Potassium bromide | 1.0 g |
| Nabox | 35.0 g |
| Water to make | 1.0 l |
| | (pH 9.8) |

The results obtained are shown as relative values in Table 2.

[Comparative Compound]

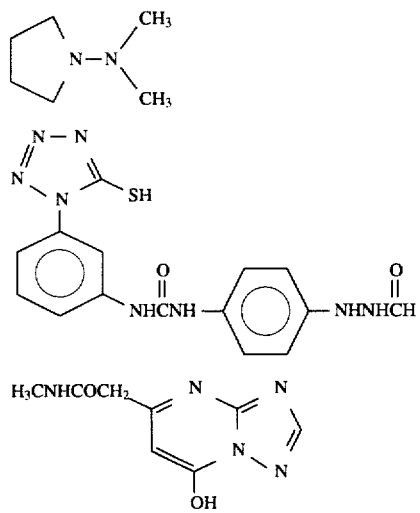

(A)

(B)

(C)

-continued
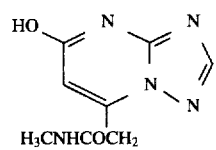 (D)
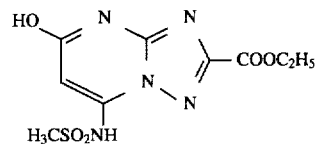 (E)
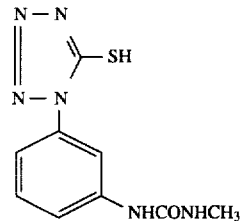 (F)
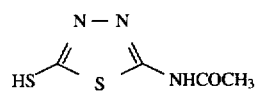 (G)
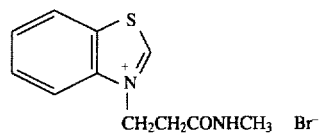 (H)
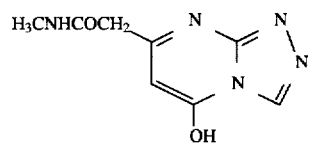 (J)
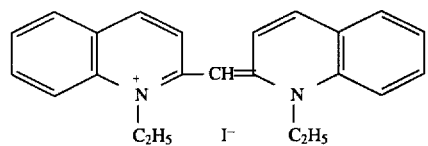 (A-8)
λmax = 578 nm
Eox = 1.07 V
(B-2)
λmax = 595 nm
Eox = 0.91 V
(B-9)
λmax = 570 nm
Eox = 0.9 V

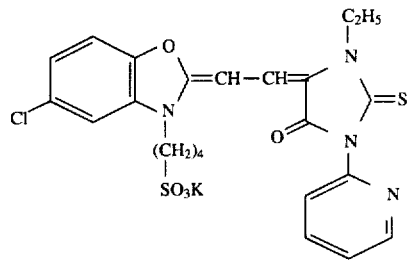
(B-12)
λmax = 500 nm
Eox = 0.9 V
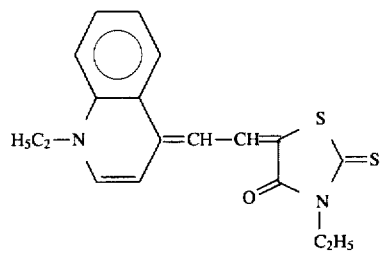
(C-3)
λmax = 660 nm
Eox = 0.5 V
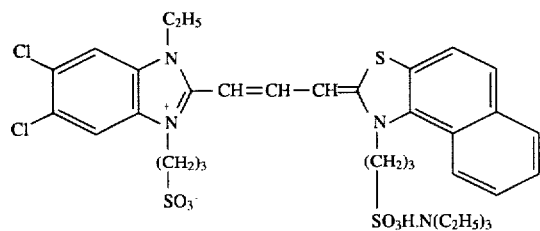
(XI-5)
λmax = 620 nm
Eox = 0.6 V
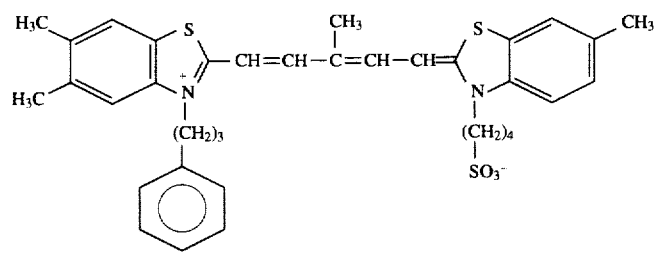
(XI-16)
λmax = 704 nm
Eox = 0.53 V
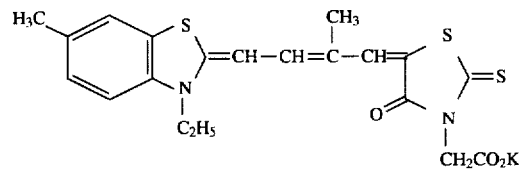
(XII-5)
λmax = 680 nm
Eox = 0.42 V
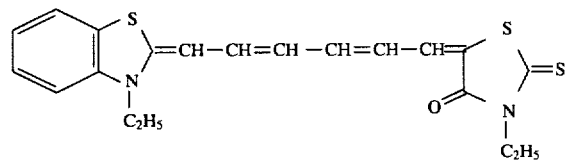
(XII-8)
λmax = 805 nm
Eox = 0.25 V
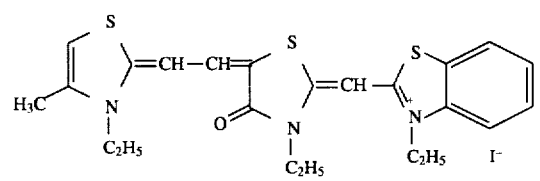
(XIII-1)
λmax = 642 nm
Eox = 0.47 V
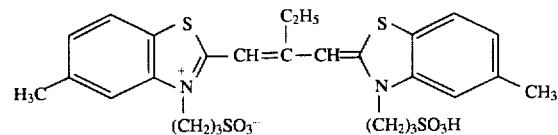
(XIV-3)
λmax = 654 nm
Eox = 0.82 V -continued

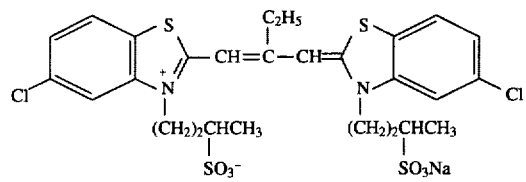

(XIV-9)

λmax = 656 nm
Eox = 0.915 V

TABLE 2

| Test No. | Sensitizing Dye and Addition Amount $10^{-4}$ mol/mol-Ag | | Oxidation Potential of Sensitizing Dye (V vs SCE) | Absorption Maximum of Sensitizing (nm) | Hydrazine Compound or Comparative Compound and Addition Amount Thereof ($10^{-4}$ mol/mol-Ag) | | Relative Sensitivity | | Fog | Remarks |
|---|---|---|---|---|---|---|---|---|---|---|
| | | | | | | | SB | SY | | |
| 1-1 | — | | — | — | — | | 100 (standard) | — | 0.03 | |
| 1-2 | (A-8) | 4.5 | 1.07 | 578 | — | | 87 | 100 (standard) | 0.03 | |
| 1-3 | " | " | " | " | (A) | 1.0 | 87 | 100 | 0.03 | Comparison |
| 1-4 | " | " | " | " | " | 150.0 | 95 | 112 | 0.06 | " |
| 1-5 | " | " | " | " | (19) | 0.3 | 87 | 123 | 0.03 | Invention |
| 1-6 | " | " | " | " | " | 1.0 | 93 | 129 | 0.03 | " |
| 1-7 | " | " | " | " | " | 3.3 | 89 | 120 | 0.03 | " |
| 1-8 | " | " | " | " | (10) | 15.0 | 89 | 115 | 0.03 | " |
| 1-9 | " | " | " | " | (F) | 0.3 | 87 | 100 | 0.03 | Comparison |
| 1-10 | " | " | " | " | " | 1.0 | 87 | 102 | 0.03 | " |
| 1-11 | " | " | " | " | " | 3.3 | 89 | 98 | 0.02 | " |
| 1-12 | " | " | " | " | (J) | 15.0 | 85 | 93 | 0.03 | Comparison |
| 1-13 | (B-2) | 3.0 | 0.91 | 595 | — | | 79 | 100 (standard) | 0.03 | |
| 1-14 | " | " | " | " | (1) | 15.0 | 81 | 182 | 0.03 | Invention |
| 1-15 | " | " | " | " | (26) | 1.0 | 81 | 162 | 0.03 | " |
| 1-16 | " | " | " | " | (A) | 1.0 | 79 | 100 | 0.04 | Comparison |
| 1-17 | " | " | " | " | " | 15.0 | 85 | 115 | 0.05 | " |
| 1-18 | " | " | " | " | " | 300.0 | 93 | 151 | 0.06 | " |
| 1-19 | " | " | " | " | (C) | 15.0 | 79 | 93 | 0.03 | Comparison |
| 1-20 | " | " | " | " | (G) | 1.0 | 71 | 85 | 0.03 | " |
| 1-21 | (B-9) | 3.0 | 0.90 | 570 | — | | 81 | 100 (standard) | 0.04 | |
| 1-22 | " | " | " | " | (19) | 1.0 | 85 | 162 | 0.04 | Invention |
| 1-23 | " | " | " | " | (14) | 15.0 | 83 | 129 | 0.04 | " |
| 1-24 | " | " | " | " | (33) | 1.5 | 81 | 128 | 0.05 | " |
| 1-25 | " | " | " | " | (A) | 1.0 | 81 | 100 | 0.04 | Comparison |
| 1-26 | " | " | " | " | " | 15.0 | 85 | 115 | 0.05 | " |
| 1-27 | " | " | " | " | " | 300.0 | 81 | 126 | 0.07 | " |
| 1-28 | " | " | " | " | (E) | 15.0 | 79 | 93 | 0.04 | Comparison |
| 1-29 | " | " | " | " | (H) | 1.5 | 72 | 83 | 0.05 | " |
| 1-30 | (B-12) | 3.0 | 0.80 | 500 | — | | 72 | 100 (standard) | 0.03 | |
| 1-31 | " | " | " | " | (1) | 15.0 | 85 | 120 | 0.03 | Invention |
| 1-33 | " | " | " | " | (13) | 15.0 | 79 | 115 | 0.03 | " |
| 1-34 | " | " | " | " | (A) | 15.0 | 79 | 107 | 0.05 | Comparison |
| 1-35 | " | " | " | " | " | 300.0 | 72 | 112 | 0.07 | " |
| 1-36 | " | " | " | " | (C) | 15.0 | 71 | 93 | 0.02 | Comparison |
| 1-37 | " | " | " | " | (B) | 15.0 | 69 | 89 | 0.03 | " |
| 1-38 | (C-3) | 3.0 | 0.50 | 660 | — | | 40 | 100 (standard) | 0.06 | |
| 1-39 | " | " | " | " | (19) | 1.0 | 66 | 191 | 0.05 | Invention |
| 1-40 | " | " | " | " | (A) | 1.0 | 45 | 117 | 0.06 | Comparison |
| 1-41 | " | " | " | " | " | 300.0 | 62 | 170 | 0.10 | " |
| 1-42 | " | " | " | " | (F) | 1.0 | 52 | 123 | 0.05 | Comparison |
| 1-43 | (XI-5) | 3.0 | 0.60 | 620 | — | | 45 | 100 (standard) | 0.05 | |
| 1-44 | " | " | " | " | (1) | 15.0 | 78 | 407 | 0.05 | Invention |
| 1-45 | " | " | " | " | (19) | 1.0 | 85 | 457 | 0.04 | " |
| 1-46 | " | " | " | " | (A) | 1.0 | 45 | 128 | 0.05 | Comparison |
| 1-47 | " | " | " | " | " | 15.0 | 52 | 186 | 0.06 | " |
| 1-48 | " | " | " | " | " | 300.0 | 83 | 372 | 0.08 | " |
| 1-49 | " | " | " | " | (C) | 15.0 | 44 | 98 | 0.05 | Comparison |

TABLE 2-continued

| Test No. | Sensitizing Dye and Addition Amount $10^{-4}$ mol/mol-Ag) | Oxidation Potential of Sensitizing Dye (V vs SCE) | Absorption Maximum of Sensitizing (nm) | Hydrazine Compound or Comparative Compound and Addition Amount Thereof ($10^{-4}$ mol/mol-Ag) | | Relative Sensitivity SB | Relative Sensitivity SY | Fog | Remarks |
|---|---|---|---|---|---|---|---|---|---|
| 1-50 | " | " | " | " | (F) | 1.0 | 52 | 117 | 0.04 | " |
| 1-51 | (XI-16) | 1.5 | 0.53 | 704 | — | | 32 | 100 (standard) | 0.04 | |
| 1-52 | " | " | " | " | (19) | 1.0 | 68 | 363 | 0.04 | Invention |
| 1-53 | " | " | " | " | (F) | 1.0 | 43 | 162 | 0.04 | Comparison |
| 1-54 | " | " | " | " | (A) | 1.0 | 36 | 138 | 0.04 | " |
| 1-55 | " | " | " | " | " | 300.0 | 65 | 229 | 0.07 | " |
| 1-56 | (XII-5) | 3.0 | 0.42 | 680 | — | | 26 | 100 (standard) | 0.04 | |
| 1-57 | " | " | " | " | (19) | 1.0 | 45 | 251 | 0.04 | Invention |
| 1-58 | " | " | " | " | (A) | 1.0 | 32 | 138 | 0.05 | Comparison |
| 1-59 | " | " | " | " | " | 300.0 | 45 | 234 | 0.07 | " |
| 1-60 | " | " | " | " | (F) | 1.0 | 27 | 131 | 0.04 | Comparison |
| 1-61 | " | " | " | " | (B) | 1.0 | 35 | 178 | 0.28 | " |
| 1-62 | (XII-8) | 3.0 | 0.25 | 805 | — | | 14 | 100 (standard) | 0.11 | |
| 1-63 | " | " | " | " | (19) | 1.0 | 32 | 251 | 0.08 | Invention |
| 1-64 | " | " | " | " | (A) | 1.0 | 20 | 132 | 0.12 | Comparison |
| 1-65 | " | " | " | " | " | 300.0 | 32 | 240 | 0.13 | " |
| 1-66 | " | " | " | " | (F) | 1.0 | 30 | 148 | 0.08 | Comparison |
| 1-67 | (XIII-1) | 3.0 | 0.47 | 642 | — | | 13 | 100 (standard) | 0.04 | |
| 1-68 | " | " | " | " | (19) | 1.0 | 35 | 417 | 0.04 | Invention |
| 1-69 | " | " | " | " | (A) | 1.0 | 21 | 117 | 0.06 | Comparison |
| 1-70 | " | " | " | " | " | 300.0 | 38 | 355 | 0.16 | " |
| 1-71 | " | " | " | " | (F) | 1.0 | 15 | 93 | 0.04 | Comparison |
| 1-72 | " | " | " | " | (B) | 1.0 | 21 | 182 | 0.26 | " |
| 1-73 | (XIV-3) | 3.0 | 0.82 | 654 | — | | 25 | 100 (standard) | 0.06 | |
| 1-74 | " | " | " | " | (1) | 10.0 | 81 | 479 | 0.06 | Invention |
| 1-75 | " | " | " | " | (10) | 10.0 | 72 | 447 | 0.07 | " |
| 1-76 | " | " | " | " | (19) | 1.0 | 85 | 513 | 0.05 | " |
| 1-77 | " | " | " | " | (26) | 1.0 | 68 | 443 | 0.06 | " |
| 1-78 | " | " | " | " | (A) | 1.0 | 27 | 107 | 0.06 | Comparison |
| 1-79 | " | " | " | " | " | 10.0 | 65 | 239 | 0.08 | " |
| 1-80 | " | " | " | " | " | 300.0 | 81 | 437 | 0.11 | " |
| 1-81 | " | " | " | " | (C) | 10.0 | 27 | 114 | 0.05 | Comparison |
| 1-82 | " | " | " | " | (J) | 10.0 | 25 | 98 | 0.06 | " |
| 1-83 | " | " | " | " | (F) | 1.0 | 47 | 93 | 0.05 | " |
| 1-84 | " | " | " | " | (G) | 1.0 | 52 | 87 | 0.06 | " |
| 1-85 | " | " | " | " | (B) | 1.0 | 46 | 269 | 0.24 | " |
| 1-86 | (XIV-9) | 3.0 | 0.915 | 656 | — | | 34 | 100 (standard) | 0.05 | |
| 1-87 | " | " | " | " | (1) | 10.0 | 81 | 417 | 0.05 | Invention |
| 1-88 | " | " | " | " | (19) | 1.0 | 83 | 457 | 0.04 | " |
| 1-89 | " | " | " | " | (26) | 1.0 | 76 | 372 | 0.05 | " |
| 1-90 | " | " | " | " | (A) | 1.0 | 39 | 100 | 0.05 | Comparison |
| 1-91 | " | " | " | " | " | 10.0 | 48 | 204 | 0.07 | " |
| 1-92 | " | " | " | " | " | 100.0 | 72 | 363 | 0.09 | " |
| 1-93 | " | " | " | " | (C) | 10.0 | 35 | 95 | 0.05 | Comparison |
| 1-94 | " | " | " | " | (F) | 1.0 | 34 | 105 | 0.04 | " |
| 1-95 | " | " | " | " | (G) | 1.0 | 28 | 83 | 0.05 | " |
| 1-96 | " | " | " | " | (B) | 1.0 | 52 | 148 | 0.27 | " |

As is clear from the results in Table 2, with the use of the compound represented by formula (I) in combination with a sensitizing dye, desensitization due to a sensitizing dye, so-called dye desensitization (SB) is improved and as a result, the spectral sensitivity (SY) increases. This effect in improvement is greater than those provided by conventional compounds such as Comparative Compound (A), i.e., a tetra-substituted hydrazine having no adsorbent group, or Comparative Compound (B), i.e., a hydrazide compound having an adsorbent group.

Also, the compounds of the present invention did not cause fog sensitization as seen in hydrazide compounds represented by Compound (B).

EXAMPLE 4

6.5 g of potassium bromide, 1.2 g of potassium iodide and 4.9 g of potassium thiocyanate were added to 1 l of an aqueous 2% gelatin solution and then thereto 0.4 l of an aqueous solution containing 57.5 g of potassium bromide and 2.5 g of potassium iodide and 0.4 l of an aqueous solution containing 85 g of silver nitrate were added with stirring at 70° C. by a double jet process at an equivalent flow rate over 45 minutes.

The mixture was cooled to 65° C. and a methanol solution of each of sensitizing dyes according to the present invention were added thereto as shown in Table 3, followed by stirring for 15 minutes.

Thereafter, an isobutene-monosodium maleate copolymer was added thereto to provide a pH of 3.8 and after water washing by sedimentation, gelatin, water and phenol were added to adjust the pH and pAg to 6.8 and 8.7, respectively. The thus-obtained silver halide grains had an average diameter of 1.64 μm and an average thickness of 0.47 μm (diameter/ thickness on average: 3.49). Then, this emulsion was ripened at 60° C. by adding thereto sodium thiosulfate pentahydrate and potassium tetraurate.

The compounds according to the present invention were added to the thus-prepared silver halide emulsion and after mixing them with stirring at 40° C., the mixtures were coated on a polyethylene terephthalate film base, which had been subjected to antistatic treatment, in thoroughly the same manner as in Example 3. The coated samples each was exposed, developed and subjected to determination of the sensitivity also in thoroughly the same manner as in Example 3 except for using a red filter (a filter capable of transmitting light having a wavelength longer than 600 nm) in place of the yellow filter used in Example 3.

The results obtained are shown in Table 3 below.

It would be understood from Table 3 that the compounds of the present invention exhibit high blue filter sensitivity (SB), high red filter sensitivity (SR) and reduced fog even in a tabular silver halide emulsion with the core being silver bromide and the shell being silver iodobromide.

TABLE 3

| Test No. | Sensitizing Dye and Addition Amount $10^{-4}$ mol/mol-Ag) | | Oxidation Potential of Sensitizing Dye (V vs SCE) | Absorption Maximum of Sensitizing (nm) | Hydrazine Compound or Comparative Compound and Addition Amount Thereof ($10^{-4}$ mol/mol-Ag) | | Relative Sensitivity | | | Remarks |
|---|---|---|---|---|---|---|---|---|---|---|
| | | | | | | | SB | SR | Fog | |
| 2-1 | — | | — | — | — | | 100 (standard) | — | 0.06 | |
| 2-2 | (XIV-7) | 3.0 | 0.91 | 654 | — | | 42 | 100 (standard) | 0.07 | |
| 2-3 | " | " | " | " | (1) | 10.0 | 72 | 389 | 0.07 | Invention |
| 2-4 | " | " | " | " | (3) | 10.0 | 69 | 380 | 0.07 | " |
| 2-5 | " | " | " | " | (10) | 10.0 | 62 | 347 | 0.07 | " |
| 2-6 | " | " | " | " | (13) | 10.0 | 63 | 339 | 0.07 | " |
| 2-7 | " | " | " | " | (19) | 1.0 | 76 | 427 | 0.06 | " |
| 2-8 | " | " | " | " | (24) | 1.0 | 69 | 407 | 0.06 | " |
| 2-9 | " | " | " | " | (26) | 1.0 | 62 | 324 | 0.07 | " |
| 2-10 | " | " | " | " | (27) | 1.0 | 62 | 309 | 0.07 | " |
| 2-11 | (XIV-7) | 3.0 | 0.91 | 654 | (A) | 1.0 | 47 | 105 | 0.07 | Comparison |
| 2-12 | " | " | " | " | " | 10.0 | 62 | 145 | 0.08 | " |
| 2-13 | " | " | " | " | " | 300.0 | 74 | 295 | 0.09 | " |
| 2-14 | " | " | " | " | (C) | 10.0 | 47 | 95 | 0.07 | Comparison |
| 2-15 | " | " | " | " | (K) | 10.0 | 49 | 105 | 0.07 | " |
| 2-16 | " | " | " | " | (J) | 10.0 | 47 | 98 | 0.07 | " |
| 2-17 | " | " | " | " | (D) | 10.0 | 49 | 93 | 0.07 | " |
| 2-18 | " | " | " | " | (F) | 1.0 | 44 | 100 | 0.06 | " |
| 2-19 | " | " | " | " | (L) | 1.0 | 42 | 98 | 0.07 | " |
| 2-20 | " | " | " | " | (G) | 1.0 | 37 | 87 | 0.07 | " |
| 2-21 | " | " | " | " | (B) | 1.0 | 42 | 107 | 0.16 | Comparison |
| 2-22 | " | " | " | " | " | 10.0 | 65 | 162 | 0.34 | " |
| 2-23 | (XIV-15) | 3.0 | 0.70 | 670 | — | | 23 | 100 (standard) | 0.09 | |
| 2-24 | " | " | " | " | (1) | 10.0 | 76 | 589 | 0.09 | Invention |
| 2-25 | " | " | " | " | (10) | 10.0 | 69 | 550 | 0.09 | " |
| 2-26 | " | " | " | " | (19) | 1.0 | 83 | 646 | 0.08 | " |
| 2-27 | " | " | " | " | (24) | 1.0 | 79 | 617 | 0.08 | " |
| 2-28 | " | " | " | " | (26) | 1.0 | 71 | 512 | 0.09 | " |
| 2-29 | " | " | " | " | (31) | 1.0 | 65 | 550 | 0.08 | " |
| 2-30 | " | " | " | " | (33) | 1.5 | 62 | 550 | 0.09 | " |
| 2-31 | (XIV-15) | 3.0 | 0.70 | 670 | (A) | 1.0 | 25 | 117 | 0.09 | Comparison |
| 2-32 | " | " | " | " | " | 10.0 | 47 | 204 | 0.09 | " |
| 2-33 | " | " | " | " | " | 300.0 | 87 | 537 | 0.10 | " |
| 2-34 | " | " | " | " | (C) | 10.0 | 25 | 129 | 0.09 | Comparison |
| 2-35 | " | " | " | " | (J) | 10.0 | 23 | 123 | 0.09 | " |
| 2-36 | " | " | " | " | (F) | 1.0 | 25 | 132 | 0.08 | " |
| 2-37 | " | " | " | " | (L) | 1.0 | 23 | 117 | 0.08 | " |
| 2-38 | " | " | " | " | (G) | 1.0 | 22 | 98 | 0.09 | " |

TABLE 3-continued

| Test No. | Sensitizing Dye and Addition Amount $10^{-4}$ mol/mol-Ag) | Oxidation Potential of Sensitizing Dye (V vs SCE) | Absorption Maximum of Sensitizing (nm) | Hydrazine Compound or Comparative Compound and Addition Amount Thereof ($10^{-4}$ mol/mol-Ag) | | Relative Sensitivity | | | Remarks |
|---|---|---|---|---|---|---|---|---|---|
| | | | | | | SB | SR | Fog | |
| 2-39 | " | " | " | " | (M) | 1.0 | 21 | 93 | 0.08 | " |
| 2-40 | " | " | " | " | (H) | 1.5 | 23 | 115 | 0.09 | " |
| 2-41 | " | " | " | " | (B) | 1.0 | 26 | 115 | 0.16 | Comparison |
| 2-42 | " | " | " | " | " | 10.0 | 31 | 93 | 0.31 | " |

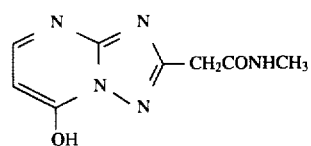

(K)

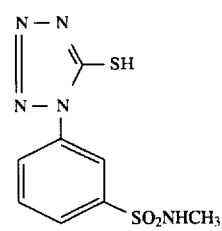

(L)

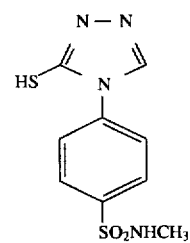

(M)

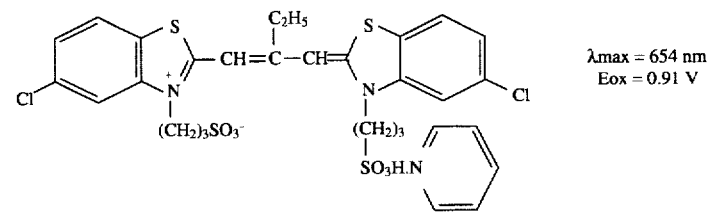

(XIV-7)

λmax = 654 nm
Eox = 0.91 V

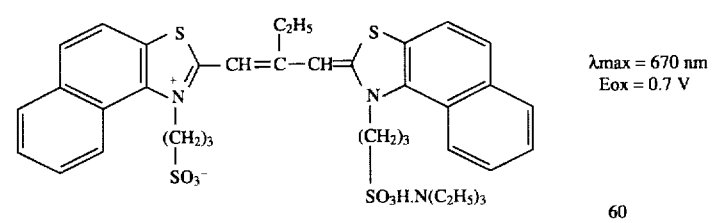

(XIV-15)

λmax = 670 nm
Eox = 0.7 V

EXAMPLE 5

Sample 101 as a multi-layer color photographic material was prepared by superimposedly coating layers each having the following composition on a cellulose triacetate film support having a subbing layer. For the purpose of comparison, Sample 100 in which Compound (19) was not added and Comparative Sample 102 in which Comparative Compound (A) was added in place of Compound (19) to each of third, fourth and fifth layers in an amount large enough to obtain an almost highest sensitivity ($3.3 \times 10^{-3}$ mol/mol-Ag to the third layer and $2.5 \times 10^{-3}$ mol/mol-Ag to the fourth and fifth layers).

(Composition of Light-Sensitive Layers)

Numerals corresponding to respective components indicate a coated amount expressed by the unit g/m² and, in the case of silver halide, a coated amount calculated in terms of silver. The coated amount for sensitizing dyes is shown by the unit mol per mol of silver halide in the same layer.

(Sample 101)
First Layer (Anti-halation Layer)

| | |
|---|---|
| Black colloidal silver | as silver 0.18 |
| Gelatin | 1.40 |

Second Layer (Interlayer)

| | |
|---|---|
| 2,5-Di-t-pentadecylhydroquinone | 0.18 |
| EX-1 | 0.070 |
| EX-3 | 0.020 |
| EX-12 | $2.0 \times 10^{-3}$ |
| U-1 | 0.060 |
| U-2 | 0.080 |
| u-3 | 0.10 |
| HBS-1 | 0.10 |
| HBS-2 | 0.020 |
| Gelatin | 1.04 |

Third Layer (First Red-Sensitive Emulsion Layer)

| | |
|---|---|
| Emulsion A | as silver 0.25 |
| Emulsion B | as silver 0.25 |
| Sensitizing Dye (XI-1) | $6.9 \times 10^{-5}$ |
| Sensitizing Dye (XIV-15) | $1.8 \times 10^{-5}$ |
| Sensitizing Dye (XIV-7) | $3.1 \times 10^{-4}$ |
| Compound (19) | $1.0 \times 10^{-4}$ |
| EX-2 | 0.34 |
| EX-10 | 0.020 |
| U-1 | 0.070 |
| U-2 | 0.050 |
| U-3 | 0.070 |
| HBS-1 | 0.060 |
| Gelatin | 0.87 |

Fourth Layer (Second Red-Sensitive Emulsion Layer)

| | |
|---|---|
| Emulsion G | as silver 1.00 |
| Sensitizing Dye (XI-1) | $5.1 \times 10^{-5}$ |
| Sensitizing Dye (XIV-15) | $1.4 \times 10^{-5}$ |
| Sensitizing Dye (XIV-7) | $2.3 \times 10^{-4}$ |
| Compound (19) | $2.3 \times 10^{-3}$ |
| EX-2 | 0.40 |
| EX-3 | 0.050 |
| EX-10 | 0.015 |
| U-1 | 0.070 |
| U-2 | 0.050 |
| U-3 | 0.070 |
| Gelatin | 1.30 |

Fifth Layer (Third Red-Sensitive Emulsion Layer)

| | |
|---|---|
| Emulsion D | as silver 1.60 |
| Sensitizing Dye (XI-1) | $5.4 \times 10^{-5}$ |
| Sensitizing Dye (XIV-15) | $1.4 \times 10^{-5}$ |
| Sensitizing Dye (XIV-7) | $2.4 \times 10^{-4}$ |
| Compound (19) | $2.4 \times 10^{-3}$ |
| EX-2 | 0.097 |
| EX-3 | 0.010 |
| EX-4 | 0.080 |
| HBS-1 | 0.22 |
| HBS-2 | 0.10 |
| Gelatin | 1.63 |

Sixth Layer (Interlayer)

| | |
|---|---|
| EX-5 | 0.040 |
| HBS-1 | 0.020 |
| Gelatin | 0.80 |

Seventh Layer (First Green-Sensitive Emulsion Layer)

| | |
|---|---|
| Emulsion A | as silver 0.15 |
| Emulsion B | as silver 0.15 |
| Sensitizing Dye (B-6) | $3.0 \times 10^{-5}$ |
| Sensitizing Dye (B-9) | $1.0 \times 10^{-4}$ |
| Sensitizing Dye (B-2) | $3.8 \times 10^{-4}$ |
| EX-1 | 0.021 |
| EX-6 | 0.26 |
| EX-7 | 0.030 |
| EX-8 | 0.025 |
| HBS-1 | 0.10 |
| HBS-3 | 0.010 |
| Gelatin | 0.63 |

Eighth Layer (Second Green-Sensitive Emulsion Layer)

| | |
|---|---|
| Emulsion C | as silver 0.45 |
| Sensitizing Dye (B-6) | $2.1 \times 10^{-5}$ |
| Sensitizing Dye (B-9) | $7.0 \times 10^{-5}$ |
| Sensitizing Dye (B-2) | $2.6 \times 10^{-4}$ |
| EX-6 | 0.094 |
| EX-7 | 0.026 |
| EX-8 | 0.018 |
| HBS-1 | 0.16 |
| HBS-3 | $8.0 \times 10^{-3}$ |
| Gelatin | 0.50 |

Ninth Layer (Third Green-Sensitive Emulsion Layer)

| | |
|---|---|
| Emulsion E | as silver 1.20 |
| Sensitizing Dye (B-6) | $3.5 \times 10^{-5}$ |
| Sensitizing Dye (B-9) | $8.0 \times 10^{-5}$ |
| Sensitizing Dye (B-2) | $3.0 \times 10^{-4}$ |
| EX-1 | 0.025 |
| EX-11 | 0.10 |
| EX-13 | 0.015 |
| HBS-1 | 0.25 |
| HBS-2 | 0.10 |
| Gelatin | 1.54 |

Tenth Layer (Yellow Filter Layer)

| | |
|---|---|
| Yellow colloidal silver | as silver 0.050 |
| EX-5 | 0.080 |
| HBS-1 | 0.030 |
| Gelatin | 0.95 |

Eleventh Layer (First Blue-Sensitive Emulsion Layer)

| | |
|---|---|
| Emulsion A | as silver 0.080 |
| Emulsion B | as silver 0.070 |
| Emulsion F | as silver 0.070 |
| Sensitizing Dye (A-2) | $3.5 \times 10^{-4}$ |
| EX-8 | 0.042 |
| EX-9 | 0.72 |
| HBS-1 | 0.28 |
| Gelatin | 1.10 |

Twelfth Layer (Second Blue-Sensitive Emulsion Layer)

| | |
|---|---|
| Emulsion G | as silver 0.45 |
| Sensitizing Dye (A-2) | $2.1 \times 10^{-4}$ |
| EX-9 | 0.15 |
| EX-10 | $7.0 \times 10^{-3}$ |
| HBS-1 | 0.050 |
| Gelatin | 0.78 |

Thirteenth Layer (Third Blue-Sensitive Emulsion Layer)

| | |
|---|---|
| Emulsion H | as silver 0.77 |
| Sensitizing Dye (A-2) | $2.2 \times 10^{-4}$ |
| EX-9 | 0.20 |
| HBS-1 | 0.070 |
| Gelatin | 0.69 |

Fourteenth Layer (First Protective Layer)

| | |
|---|---|
| Emulsion I | as silver 0.20 |
| U-4 | 0.11 |
| u-5 | 0.17 |
| HBS-1 | $5.0 \times 10^{-2}$ |
| Gelatin | 1.00 |

Fifteenth Layer (Second Protective Layer)

| | |
|---|---|
| H-1 | 0.40 |
| B-1 (diameter: 1.7 μm) | $5.0 \times 10^{-2}$ |
| B-2 (diameter: 1.7 μm) | 0.10 |
| B-3 | 0.10 |

-continued

| | |
|---|---|
| S-1 | 0.20 |
| Gelatin | 1.20 |

Further, in order to improve preservability, processing property, pressure resistance, antimold and antifungal property, antistatic property and coatability, W-1, W-2, W-3, B-4, B-5, F-1, F-2, F-3, F-4, F-5, F-6, F-7, F-8, F-9, F-10, F-11, F-12, F-13, iron salt, lead salt, gold salt, platinum salt, iridium salt and rhodium salt were added to each layer.

TABLE 4

| | Average AgI Content (%) | Average Grain Size (μm) | Coefficient of Fluctuation in Grain size (%) | Diameter/ Thickness Ratio | Silver Amount Ratio (AgI content: %) |
|---|---|---|---|---|---|
| Emulsion A | 4.0 | 0.45 | 27 | 1 | core/shell = ⅓ (¹³⁄₁), double structure grain |
| Emulsion B | 8.9 | 0.70 | 14 | 1 | core/shell = 3/7 (25/2), double structure grain |
| Emulsion C | 10 | 0.75 | 30 | 2 | core/shell = ½ (²⁴⁄₃), double structure grain |
| Emulsion D | 16 | 1.05 | 35 | 2 | core/shell = ⅚ (⁴⁰⁄₀), double structure grain |
| Emulsion E | 10 | 1.05 | 35 | 3 | core/shell = ½ (²⁴⁄₃), double structure grain |
| Emulsion F | 4.0 | 0.25 | 28 | 1 | core/shell = ⅓ (¹³⁄₁), double structure grain |
| Emulsion G | 14.0 | 0.75 | 25 | 2 | core/shell = ½ (⁴²⁄₀), double structure grain |
| Emulsion H | 14.5 | 1.30 | 25 | 3 | core/shell = ³⁷⁄₆₃ (³⁴⁄₃), double structure grain |
| Emulsion I | 1 | 0.07 | 15 | 1 | uniform grain |

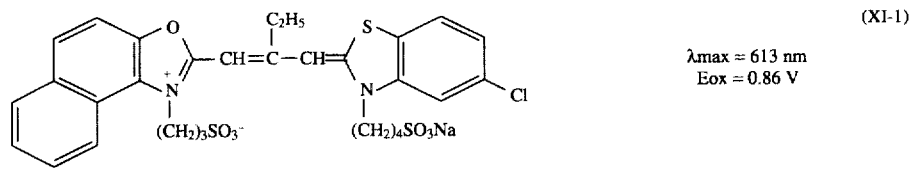

(XI-1)

λmax = 613 nm
Eox = 0.86 V

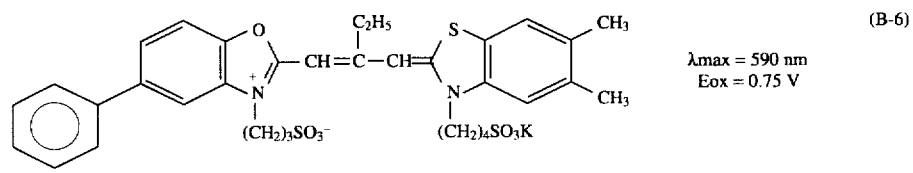

(B-6)

λmax = 590 nm
Eox = 0.75 V

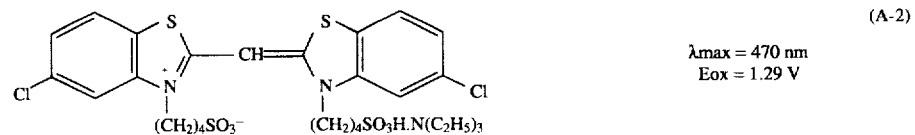

(A-2)

λmax = 470 nm
Eox = 1.29 V

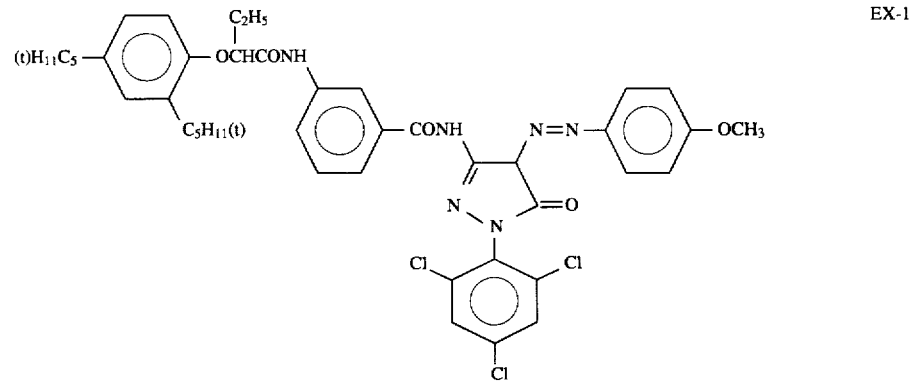

EX-1

-continued
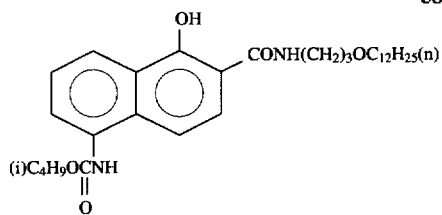
EX-2
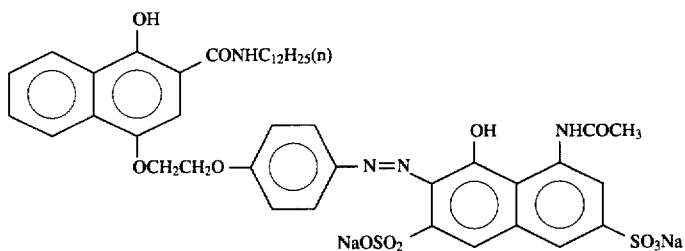
EX-3
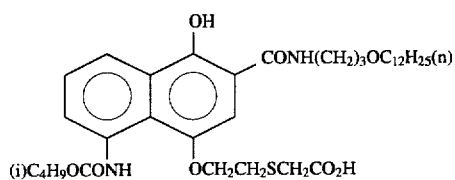
EX-4
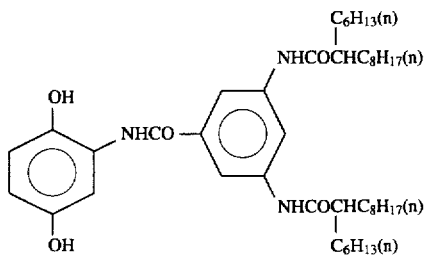
EX-5
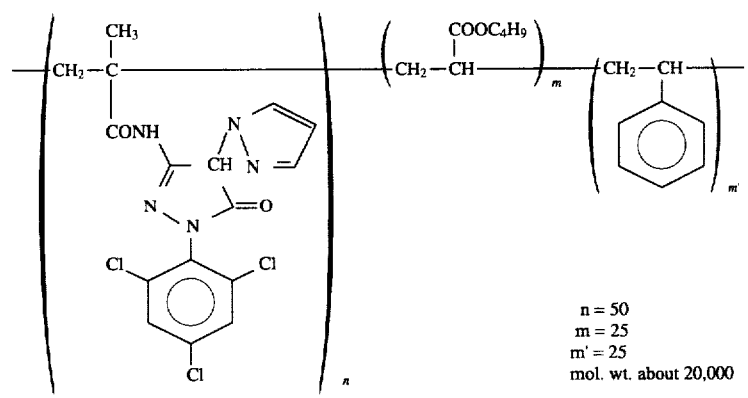
EX-6
n = 50
m = 25
m' = 25
mol. wt. about 20,000
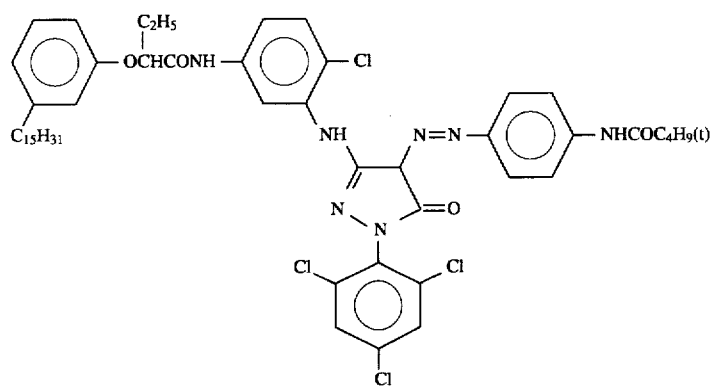
EX-7

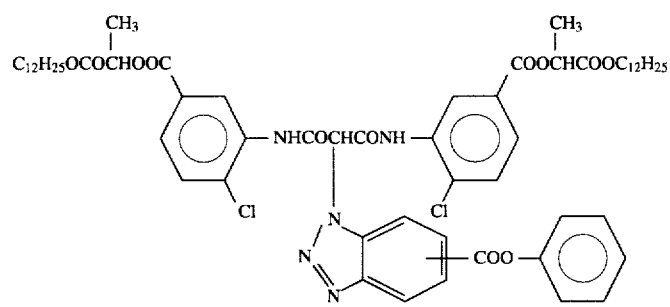
EX-8
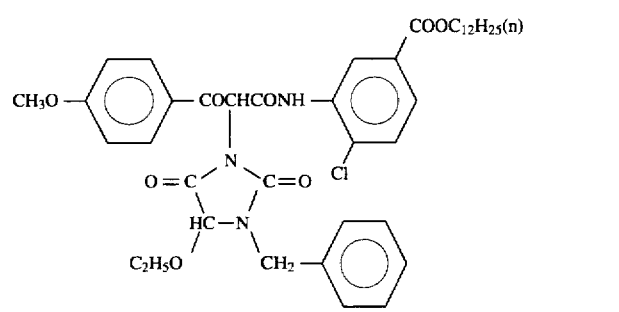
EX-9
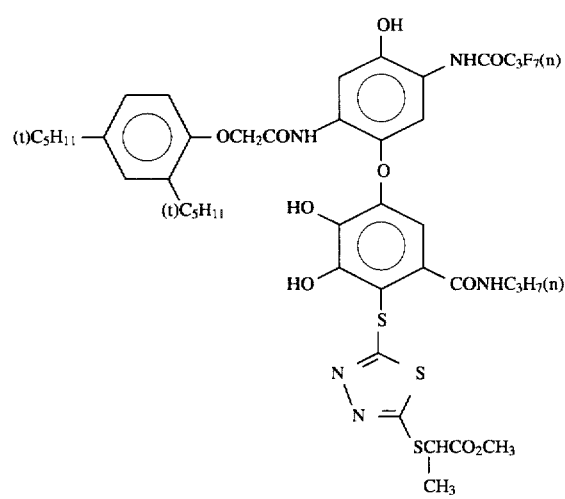
EX-10
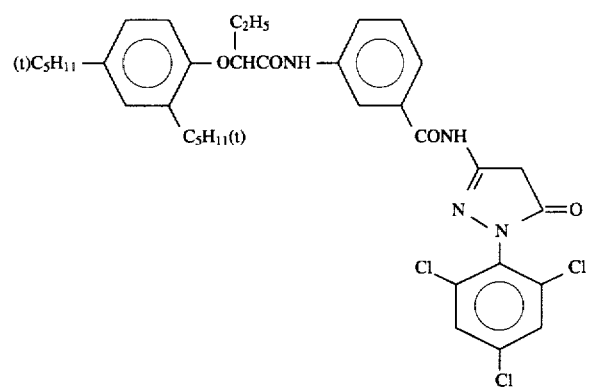
EX-11

-continued
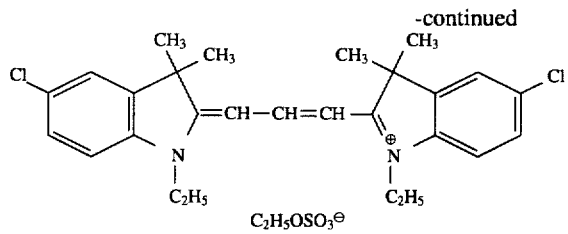 EX-12
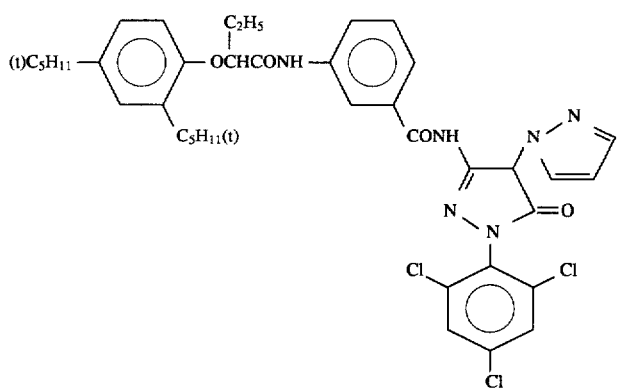 EX-13
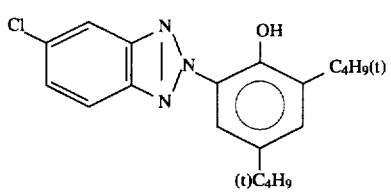 U-1
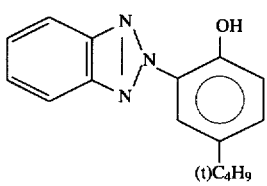 U-2
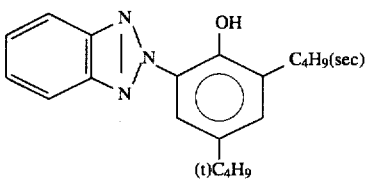 U-3
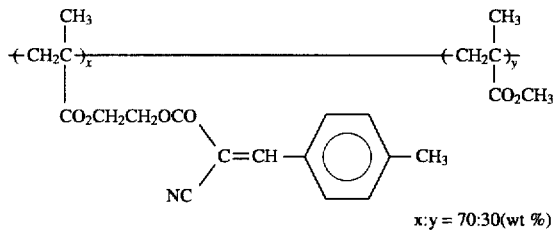 U-4
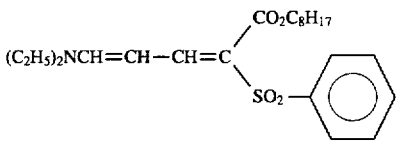 U-5
Tricresyl phosphate    HBS-1
Di-n-butyl phthalate    HBS-2

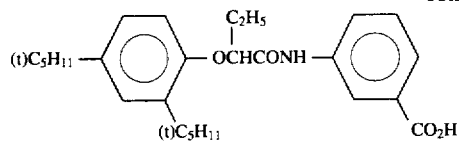 HBS-3
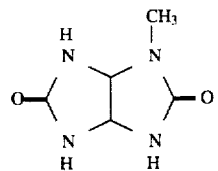 S-1
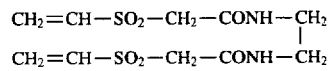 H-1
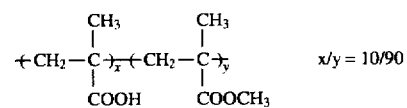 x/y = 10/90  BP-1
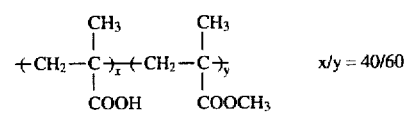 x/y = 40/60  BP-2
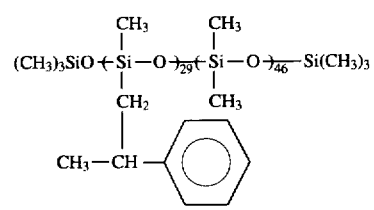 BP-3
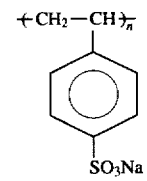 BP-4
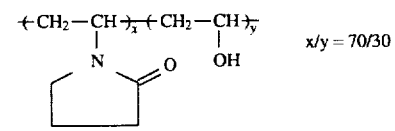 x/y = 70/30  BP-5
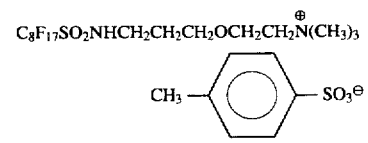 W-1
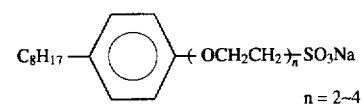 n = 2~4  W-2
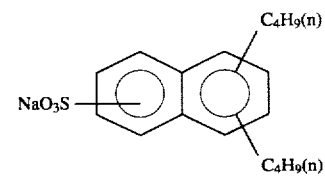 W-3

-continued
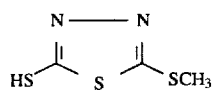 F-1
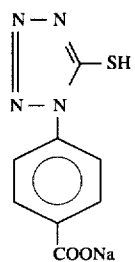 F-2
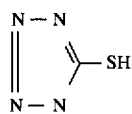 F-3
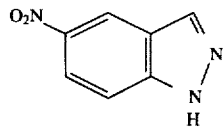 F-4
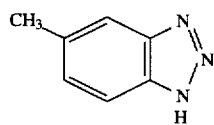 F-5
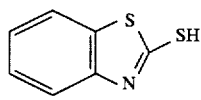 F-6
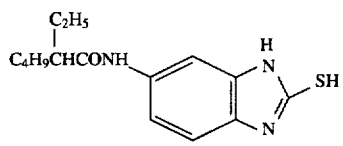 F-7
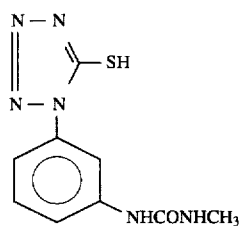 F-8
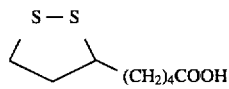 F-9
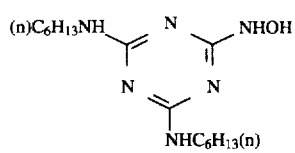 F-10

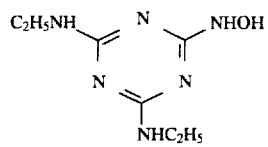

F-11

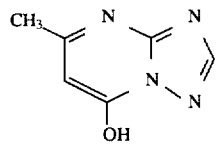

F-12

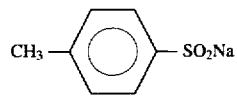

F-13

Each of these samples was exposed for 1/100 second through a continuous wedge using a red filter (a filter capable of transmitting light having a wavelength longer than 600 nm), developed with the following processing solutions and subjected to determination of the density. The standard point of the optical density in determining the sensitivity was [fog+0.1] and the sensitivities are shown in Table 5 by a relative value with the relative sensitivity of Sample 100, in which neither Compound (19) nor Comparative Compound (A) was used, being taken as 100.

Also, the increase in fog is shown by the difference from the fog of Sample 100 free of Compound (19) or Comparative Compound (A).

Processing Procedure

| Step | Processing Time | Processing Temperature (°C.) | Replenishing Amount (ml) | Tank Volume (l) |
| --- | --- | --- | --- | --- |
| Color Development | 2 min. 45 sec. | 38 | 33 | 20 |
| Bleaching | 6 min. 30 sec. | 38 | 25 | 40 |
| Washing | 2 min. 10 sec. | 24 | 1,200 | 20 |
| Fixing | 4 min. 20 sec. | 38 | 25 | 30 |
| Washing (1) | 1 min. 05 sec. | 24 | Co-current piping system from (2) to (1) | 10 |
| Washing (2) | 1 min. 00 sec. | 24 | 1,200 | 10 |
| Stabilization | 1 min. 05 sec. | 38 | 25 | 10 |
| Drying | 4 min. 20 sec. | 55 | | |

The replenishing amount was per 1-m length in 35-mm width.

The compositions of the processing solutions are shown below.

| | Mother Solution (g) | Replenisher (g) |
| --- | --- | --- |
| (Color Developer) | | |
| Diethylenetriaminepenta-acetic acid | 1.0 | 1.1 |
| 1-Hydroxyethylidene-1,1-diphosphonic acid | 3.0 | 3.2 |
| Sodium sulfite | 4.0 | 4.4 |
| Potassium carbonate | 30.0 | 37.0 |
| Potassium bromide | 1.4 | 0.7 |
| Potassium iodide | 1.5mg | — |
| Hydroxylamine sulfate | 2.4 | 2.8 |

-continued

| | Mother Solution (g) | Replenisher (g) |
| --- | --- | --- |
| 4-[N-Ethyl-N-β-hydroxy-ethylamino]-2-methylaniline sulfate | 4.5 | 5.5 |
| Water to make | 1.0 l | 1.0 l |
| pH | 10.05 | 10.10 |
| (Bleaching Solution) | | |
| Sodium ethylenediamine-tetraacetato ferrite trihydrate | 100.0 | 120.0 |
| Disodium ethylenediamine- | 10.0 | 11.0 |

-continued

| | Mother Solution (g) | Replenisher (g) |
| --- | --- | --- |
| tetraacetate | | |
| Ammonium bromide | 140.0 | 160.0 |
| Ammonium nitrate | 30.0 | 35.0 |
| Aqueous ammonia (27%) | 6.5ml | 4.0ml |
| Water to make | 1.0 l | 1.0 l |
| pH | 6.0 | 5.7 |
| (Fixing Solution) | | |
| Sodium ethylenediamine-tetraacetate | 0.5 | 0.7 |
| Sodium sulfite | 7.0 | 8.0 |
| Sodium bisulfite | 5.0 | 5.5 |
| Ammonium thiosulfate (70% aq. sol.) | 170.0ml | 200.0ml |
| Water to make | 1.0 l | 1.0 l |
| pH | 6.7 | 6.6 |

-continued

|  | Mother Solution (g) | Replenisher (g) |
|---|---|---|
| (Stabilizing Solution) | | |
| Formaldehyde (37%) | 2.0 ml | 3.0 ml |
| Polyoxyethylene-p-monononyl-phenyl ether (average polymerization degree: 10) | 0.3 | 0.45 |
| Disodium ethylenediamine-tetraacetate | 0.05 | 0.08 |
| Water to make | 1.0 l | 1.0 l |
| pH | 5.0–8.0 | 5.8–8.0 |

TABLE 5

| Sample No. | Compound or Comparative Compound | Relative Sensitivity | Increase in Fog | Remarks |
|---|---|---|---|---|
| 100 | — | 100 (standard) | — | |
| 101 | (19) | 129 | 0.02 | Invention |
| 102 | (A) | 117 | 0.05 | Comparison |

It would be understood that the sample using the compound of the present invention can have increased spectral sensitivity.

The increase in spectral sensitivity is larger than that in the sample using Comparative Compound (A), and the fog is also reduced.

EXAMPLE 6

The coated samples prepared in Example 4 under test numbers (2—2) to (2–13), (2–21) and (2–22) were allowed to stand at room temperature for one year and then subjected to exposure, development and determination of the red filter sensitivity and the fog in thoroughly the same manner as in Example 4.

TABLE 6

| Sample No. | Sensitivity and Fog after One Year Leaving at –30° C. under Sealing of Argon Gas | | Sensitivity and Fog after One Year Leaving at Room Temperature | | Remarks |
|---|---|---|---|---|---|
| | Relative Red Sensitivity ($S_R$) | Fog | Relative Red Sensitivity ($S_R$) | Fog | |
| 2-2 | 100 (standard) | 0.07 | 83 | 0.08 | |
| 2-3 | 380 | 0.07 | 372 | 0.07 | Invention |
| 2-4 | 380 | 0.07 | 354 | 0.07 | " |
| 2-5 | 347 | 0.07 | 339 | 0.08 | " |
| 2-6 | 339 | 0.06 | 316 | 0.06 | " |
| 2-7 | 427 | 0.06 | 427 | 0.06 | " |
| 2-8 | 407 | 0.07 | 398 | 0.07 | " |
| 2-9 | 324 | 0.07 | 324 | 0.07 | " |
| 2-10 | 316 | 0.07 | 302 | 0.08 | " |
| 2-11 | 105 | 0.07 | 95 | 0.09 | Comparison |
| 2-12 | 151 | 0.09 | 129 | 0.12 | " |
| 2-13 | 295 | 0.10 | 369 | 0.14 | " |
| 2-21 | 107 | 0.16 | 117 | 0.27 | " |
| 2-22 | 178 | 0.35 | 155 | 0.51 | " |

It would be further understood from Table 6 that the samples according to the present invention exhibited very small reduction in sensitivity as well as very low increase in fog after storage at room temperature for one year, which reveals to be an excellent technique.

From the foregoing, it is confirmed that the compounds of the present invention, of which synthesis examples are described in Examples 1 and 2, provide a silver halide photographic material realizing high sensitivity but no increase in fog.

The compounds of the present invention are extremely useful compounds for achieving a highly sensitive silver halide photographic material.

While the invention has been described in detail and with reference to specific embodiments thereof, it will be apparent to one skilled in the art that various changes and modifications can be made therein without departing from the spirit and scope thereof.

What is claimed is:

1. A silver halide photographic material comprising a support having thereon a silver halide emulsion layer which comprises a hydrazine compound having at least one adsorbent group to silver halide, wherein said hydrazine compound is represented by formula (I)

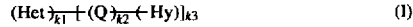

(I)

wherein Het represents a group having a 5-, 6- or 7-membered heterocyclic ring which contains at least one nitrogen atom and may contain a hetero atom other than a nitrogen atom, Q represents a divalent linking group selected from the group consisting of a sulfur atom, an oxygen atom and an atomic group containing at least one of a carbon atom, a nitrogen atom, a sulfur atom and an oxygen atom, Hy represents an atomic group having a hydrazine structure represented by formula (II), k1 and k3 each represents 1, 2, 3 or 4, and k2 represents 0 or 1;

(II)

wherein $R_1$, $R_2$, $R_3$ and $R_4$ each represents an alkyl group, an aryl group or a heterocyclic group, or $R_1$ and $R_2$, $R_3$ and $R_4$, $R_1$ and $R_3$, or $R_2$ and $R_4$ can combine with each other to form a ring other than an aromatic ring.

2. The silver halide photographic material as claimed in claim 1, wherein the silver halide emulsion layer contains a silver halide emulsion which is spectrally sensitized.

3. The silver halide photographic material as claimed in claim 1, wherein the moiety represented by formula (II) is a moiety represented by formulae (III), (IV) or (V);

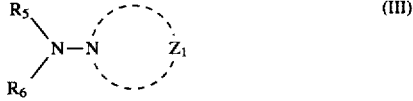

(III)

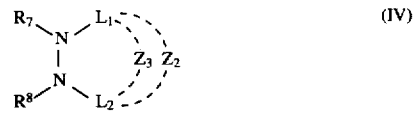

(IV)

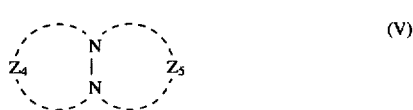

(V)

wherein $R_5$, $R_6$, $R_7$ and $R_8$ each represents an alkyl group, an aryl group or a heterocyclic group, $Z_1$ represents an alkylene group having 4 or 6 carbon atoms, $Z_3$ represents an alkylene group having 1 or 2 carbon atoms, $Z_4$ and $Z_5$ each represents an alkylene group having 3 carbon atoms, $L_1$ and $L_2$ each represents a methine group.

4. The silver halide photographic material as claimed in claim 1, wherein $R_1$, $R_2$, $R_3$ and $R_4$ each represents an alkyl group, and $R_1$ and $R_2$, $R_3$ and $R_4$, $R_1$ and $R_3$, or $R_2$ and $R_4$ combine together to form an alkylene group containing no atom other than a carbon atom as the constituent of the ring.

5. The silver halide photographic material as claimed in claim 1, wherein $R_1$, $R_2$, $R_3$ and $R_4$ each represents a group which contains an unsubstituted methylene group or a methylene group substituted by an alkyl group, with a methylene carbon atom of said substituted or unsubstituted methylene being directly bonded to a nitrogen atom of hydrazine.

6. The silver halide photographic material as claimed in claim 1, wherein Het represents a nitrogen-containing heterocyclic moiety represented by formula (VI), (VII), (VIII), (IX), (X), (XI) or (XII):

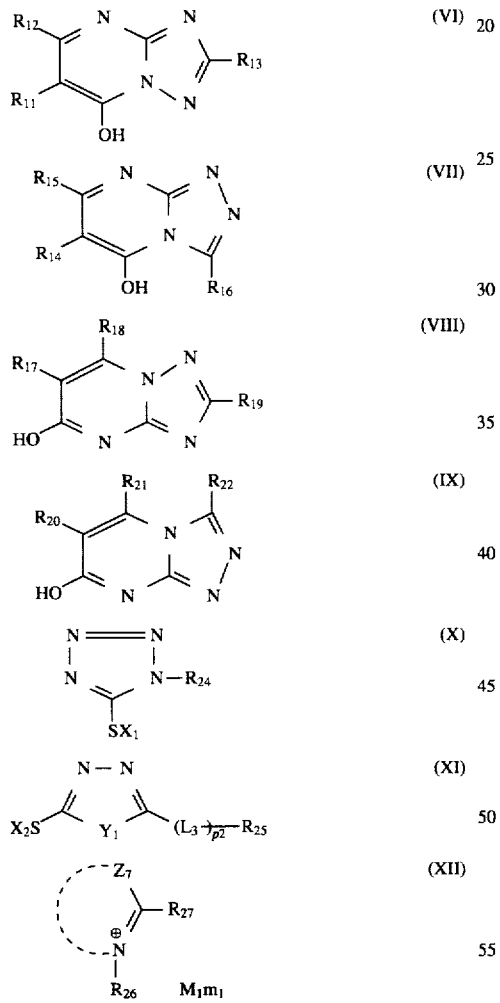

wherein $R_{11}$, $R_{12}$, $R_{13}$, $R_{14}$, $R_{15}$, $R_{16}$, $R_{17}$, $R_{18}$, $R_{19}$, $R_{20}$, $R_{21}$ and $R_{22}$ each represents a hydrogen atom or a monovalent substituent; $R_{24}$ represents an alkyl group, an aryl group or a heterocyclic group; $X_1$ represents a hydrogen atom, an alkali metal atom, an ammonium group or a precursor; $Y_1$ represents an oxygen atom, a sulfur atom, =NH, or =N—$(L_4)_{p^3}$—$R_{28}$; $L_3$ and $L_4$ each represents a divalent linking group; $R_{25}$ and $R_{28}$ each represents a hydrogen atom, an alkyl group, an aryl group or a heterocyclic group; $X_2$ has the same meaning as $X_1$; p2 and p3 each represents an integer of 0 or one; $Z_7$ represents an atomic group necessary for forming a 5- or 6-membered nitrogen atom-containing heterocyclic ring; and $R_{26}$ and $R_{27}$ each represents a hydrogen atom or an alkyl group.

7. The silver halide photographic material as claimed in claim 6, wherein said monovalent substituent is a $C_1$–$C_4$ alkyl group, a carboxyl group, an alkoxy group, an aralkyl group, an aryl group, a heterocyclic group, an alkylthio group, an arylthio group, an aryloxy group, an alkylamino group having 3 or more carbon atoms, an arylamino group, a halogen atom,

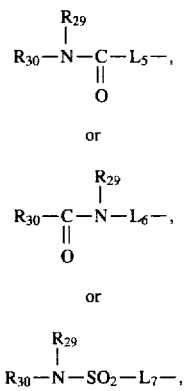

wherein $L_5$, $L_6$ and $L_7$ each is an alkylene group and $R_{29}$ and $R_{30}$ may be the same or different and each represents a hydrogen atom, and alkyl group, an aralkyl group, and aryl group, or a heterocyclic group.

8. The silver halide photographic material as claimed in claim 1, wherein Q represents a divalent linking group having 20 or less carbon atoms and composed of a combination of one or more of an alkylene group; an arylene group; an alkenylene group; an amide group; an ester group; a sulfoamide group; a sulfonic acid ester group; a ureido group; a sulfonyl group; a sulfinyl group; a thioether group; an ether group; a carbonyl group; —$N(R^1)$— wherein $R^1$ represents a hydrogen atom, an alkyl group or an aryl group; and a heterocyclic divalent group.

9. The silver halide photographic material as claimed in claim 1, wherein Q represents an ester group or an amide group.

10. The silver halide photographic material as claimed in claim 1, wherein k1 and k3 each is 1 or 2.

11. The silver halide photographic material as claimed in claim 1, wherein k2 and k3 each is 1.

12. The silver halide photographic material as claimed in claim 1, wherein said hydrazine compound is present in a silver halide emulsion in an amount of $1 \times 10^{-9}$ to $5 \times 10^{-1}$ mol per mol of silver halide.

13. The silver halide photographic material as claimed in claim 1, wherein at least one of said alkyl group, aryl group and heterocyclic group is unsubstituted.

14. The silver halide photographic material as claimed in claim 1, wherein at least one of said alkyl group, aryl group and heterocyclic group is substituted by a substituent selected from the group consisting of a carboxyl group, a sulfo group, a cyano group, a halogen atom, a hydroxyl group, an alkoxycarbonyl group, an alkoxy group, an aryloxy group, an acyloxy group, an acyl group, a carbamoyl group, a sulfamoyl group, an aryl group, a heterocyclic group, an amino group, an alkylthio group, an alkylsulfonyl group, an alkylsulfinyl group, a nitro group, a phosphate group, an acylamino group, an ammonium group, a mercapto group, a hydrazino group, a ureido group, an imide group, and an unsaturated hydrocarbon group.

* * * * *